(12) United States Patent
Neville et al.

(10) Patent No.: US 9,012,511 B2
(45) Date of Patent: Apr. 21, 2015

(54) NANOPARTICULATE CINACALCET COMPOSITIONS

(75) Inventors: Deborah Neville, Lower Gwynedd, PA (US); Scott Jenkins, Downingtown, PA (US); David Manser, Longford (IE)

(73) Assignee: Alkermes Pharma Ireland Limited, Dublin (IE)

(*) Notice: Subject to any disclaimer, the term of this patent is extended or adjusted under 35 U.S.C. 154(b) by 349 days.

(21) Appl. No.: 13/110,647

(22) Filed: May 18, 2011

(65) Prior Publication Data

US 2011/0287065 A1    Nov. 24, 2011

Related U.S. Application Data

(60) Provisional application No. 61/346,331, filed on May 19, 2010.

(51) Int. Cl.
| | | |
|---|---|---|
| A01N 33/02 | (2006.01) | |
| A01N 33/24 | (2006.01) | |
| A61K 31/13 | (2006.01) | |
| A61K 31/135 | (2006.01) | |
| A61K 9/14 | (2006.01) | |
| A61K 9/16 | (2006.01) | |
| A61K 9/50 | (2006.01) | |
| A61K 31/137 | (2006.01) | |
| A61K 9/10 | (2006.01) | |
| A61K 9/51 | (2006.01) | |

(52) U.S. Cl.
CPC ............... *A61K 31/137* (2013.01); *A61K 9/10* (2013.01); *A61K 9/5138* (2013.01); *A61K 9/5146* (2013.01); *A61K 9/5161* (2013.01); *A61K 9/5192* (2013.01)

(58) Field of Classification Search
USPC ........................................... 514/655
See application file for complete search history.

(56) References Cited

U.S. PATENT DOCUMENTS

| | | |
|---|---|---|
| 4,783,484 A | 11/1988 | Violante et al. |
| 4,826,689 A | 5/1989 | Violanto et al. |
| 4,997,454 A | 3/1991 | Violante et al. |
| 5,145,684 A | 9/1992 | Liversidge et al. |
| 5,298,262 A | 3/1994 | Na et al. |
| 5,302,401 A | 4/1994 | Liversidge et al. |
| 5,336,507 A | 8/1994 | Na et al. |
| 5,340,564 A | 8/1994 | Illig et al. |
| 5,346,702 A | 9/1994 | Na et al. |
| 5,352,459 A | 10/1994 | Hollister et al. |
| 5,429,824 A | 7/1995 | June |
| 5,470,583 A | 11/1995 | Na et al. |
| 5,510,118 A | 4/1996 | Bosch et al. |
| 5,518,187 A | 5/1996 | Bruno et al. |
| 5,534,270 A | 7/1996 | De Castro |
| 5,543,133 A | 8/1996 | Swanson et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,622,938 A | 4/1997 | Wong |
| 5,662,883 A | 9/1997 | Bagchi et al. |
| 5,665,331 A | 9/1997 | Bagchi et al. |
| 5,718,388 A | 2/1998 | Czekai et al. |
| 5,834,025 A | 11/1998 | De Garavilla et al. |
| 5,862,999 A | 1/1999 | Czekai et al. |
| 6,011,068 A | 1/2000 | Nemeth et al. |
| 6,031,003 A | 2/2000 | Nemeth et al. |
| 6,211,244 B1 | 4/2001 | Van Wagenen et al. |
| 6,264,922 B1 | 7/2001 | Wood et al. |
| 6,267,989 B1 | 7/2001 | Liversidge et al. |
| 6,270,806 B1 | 8/2001 | Liversidge et al. |
| 6,313,146 B1 | 11/2001 | Van Wagenen et al. |
| 6,316,029 B1 | 11/2001 | Jain et al. |
| 6,375,986 B1 | 4/2002 | Ryde et al. |
| 6,406,718 B1 | 6/2002 | Cooper |
| 6,428,814 B1 | 8/2002 | Bosch |
| 6,431,478 B1 | 8/2002 | Reed et al. |
| 6,432,381 B2 | 8/2002 | Liversidge et al. |
| 6,582,285 B2 | 6/2003 | Czekai et al. |
| 6,592,903 B2 | 7/2003 | Ryde et al. |
| 6,742,734 B2 | 6/2004 | Reed et al. |
| 6,745,962 B2 | 6/2004 | Reed et al. |
| 6,811,767 B1 | 11/2004 | Bosch et al. |
| 6,908,626 B2 | 6/2005 | Cooper et al. |
| 6,969,529 B2 | 11/2005 | Bosch et al. |
| 6,976,647 B2 | 12/2005 | Reed et al. |
| 6,991,191 B2 | 1/2006 | Reed et al. |
| 7,198,795 B2 | 4/2007 | Cooper et al. |
| 7,244,451 B2 | 7/2007 | Bosch et al. |
| 7,288,267 B2 | 10/2007 | Bosch et al. |

(Continued)

FOREIGN PATENT DOCUMENTS

| | | |
|---|---|---|
| WO | WO 97/14407 | 4/1997 |
| WO | WO 2009/002427 A2 | 12/2008 |

OTHER PUBLICATIONS

International Search Report and Written Opinion cited in related International Patent Application No. PCT/US2011/036949, completed May 29, 2012.

(Continued)

*Primary Examiner* — Michael B Pallay
(74) *Attorney, Agent, or Firm* — Foley & Lardner LLP

(57) ABSTRACT

Described are compositions of stable nanoparticulate cinacalcet or a salt thereof, and methods of making and using them. The compositions exhibit an improved dissolution rate, improved bioavailability, and reduced difference in absorption when administered orally under fed as compared to fasting conditions.

17 Claims, 1 Drawing Sheet

(56) References Cited

U.S. PATENT DOCUMENTS

| | | | |
|---|---|---|---|
| 7,320,802 B2 | 1/2008 | Ryde et al. | |
| 7,390,505 B2 | 6/2008 | Gustow et al. | |
| 7,459,283 B2 | 12/2008 | Wertz et al. | |
| 7,521,068 B2 | 4/2009 | Bosch et al. | |
| 7,695,739 B2 | 4/2010 | Cooper et al. | |
| 7,713,551 B2 | 5/2010 | McGurk et al. | |
| 7,763,278 B2 | 7/2010 | Cooper et al. | |
| 7,825,087 B2 | 11/2010 | Jenkins et al. | |
| 7,842,232 B2 | 11/2010 | Bosch et al. | |
| 7,850,995 B2 | 12/2010 | Bosch et al. | |
| 7,879,360 B2 | 2/2011 | Cunningham et al. | |
| 7,910,577 B2 | 3/2011 | Liversidge et al. | |
| 7,927,627 B2 | 4/2011 | Ryde et al. | |
| 7,931,917 B2 | 4/2011 | Ryde et al. | |
| 2001/0053664 A1 | 12/2001 | Czekai et al. | |
| 2002/0012675 A1 | 1/2002 | Jain et al. | |
| 2002/0179758 A1 | 12/2002 | Reed et al. | |
| 2003/0023203 A1 | 1/2003 | Lavi et al. | |
| 2003/0087308 A1 | 5/2003 | Lindner et al. | |
| 2003/0108616 A1 | 6/2003 | Bosch et al. | |
| 2003/0137067 A1 | 7/2003 | Cooper et al. | |
| 2003/0185869 A1 | 10/2003 | Wertz et al. | |
| 2003/0215502 A1 | 11/2003 | Pruss et al. | |
| 2004/0105778 A1 | 6/2004 | Lee et al. | |
| 2004/0105889 A1 | 6/2004 | Ryde et al. | |
| 2004/0115134 A1 | 6/2004 | Merisko-Liversidge | |
| 2004/0173696 A1 | 9/2004 | Cunningham et al. | |
| 2004/0195413 A1 | 10/2004 | Reed et al. | |
| 2004/0258757 A1 | 12/2004 | Bosch et al. | |
| 2005/0031691 A1 | 2/2005 | McGurk et al. | |
| 2005/0147664 A1 | 7/2005 | Liversidge et al. | |
| 2005/0238725 A1 | 10/2005 | Cunningham et al. | |
| 2007/0110776 A1 | 5/2007 | Cooper et al. | |
| 2007/0141159 A1 | 6/2007 | Bosch et al. | |
| 2007/0249520 A1* | 10/2007 | Gore et al. | 514/2 |
| 2008/0003295 A1 | 1/2008 | Bosch et al. | |
| 2008/0025807 A1 | 1/2008 | Reed et al. | |
| 2008/0124393 A1 | 5/2008 | Swanson et al. | |
| 2008/0152585 A1 | 6/2008 | Ryde et al. | |
| 2008/0171091 A1 | 7/2008 | Wood et al. | |
| 2008/0213374 A1 | 9/2008 | Carty et al. | |
| 2008/0213378 A1 | 9/2008 | Cooper et al. | |
| 2008/0220074 A1 | 9/2008 | Bosch et al. | |
| 2008/0226734 A1 | 9/2008 | Jenkins et al. | |
| 2008/0248123 A1 | 10/2008 | Swanson et al. | |
| 2008/0254114 A1 | 10/2008 | Jenkins et al. | |
| 2008/0279929 A1 | 11/2008 | Devane et al. | |
| 2008/0317843 A1 | 12/2008 | Jenkins et al. | |
| 2009/0035366 A1 | 2/2009 | Liversidge et al. | |
| 2009/0074873 A1 | 3/2009 | Wood et al. | |
| 2009/0155331 A1 | 6/2009 | Ruddy et al. | |
| 2009/0238884 A1 | 9/2009 | Liversidge et al. | |
| 2009/0252807 A1 | 10/2009 | Jenkins et al. | |
| 2009/0269400 A1 | 10/2009 | Devane et al. | |
| 2009/0291142 A1 | 11/2009 | Jenkins et al. | |
| 2009/0297596 A1 | 12/2009 | Devane et al. | |
| 2009/0304801 A1 | 12/2009 | Liversidge et al. | |
| 2010/0028439 A1 | 2/2010 | Jenkins et al. | |
| 2010/0221327 A1 | 9/2010 | Jenkins et al. | |
| 2010/0247636 A1 | 9/2010 | Devane et al. | |
| 2010/0260858 A1 | 10/2010 | Ruddy et al. | |
| 2010/0260859 A1 | 10/2010 | Ruddy et al. | |
| 2010/0316725 A1 | 12/2010 | Ryde et al. | |
| 2011/0008435 A1 | 1/2011 | Devane et al. | |
| 2011/0027371 A1 | 2/2011 | Cooper et al. | |
| 2011/0064803 A1 | 3/2011 | Devane et al. | |

OTHER PUBLICATIONS

Lindahl et al., "Characterization of Fluids from the Stomach and Proximal Jejunum in Men and Woman," *Pharmaceutical Research*, pp. 497-502 (1997).

Gupta, "Fundamentals of Drug Nanoparticles," pp. 1-19, (2006).

Torres, "Cinacalcet HC1: a novel treatment for secondary hyperparathyroidism caused by chronic kidney disease". *Journal of Renal Nutrition*, vol. 16, No. 3, pp. 253-258 (2006).

Padhi et al., "The Pharmacokinetics of Cinacalcet are Unaffected Following Consumption of High- and Low-Fat Meals," *American J. of Therapeutics*, vol. 14, pp. 235-240 (2007).

Food and Drug Administration, Science and Research, Nanotechnology Task Force Report, 2007, 18 pages.

* cited by examiner

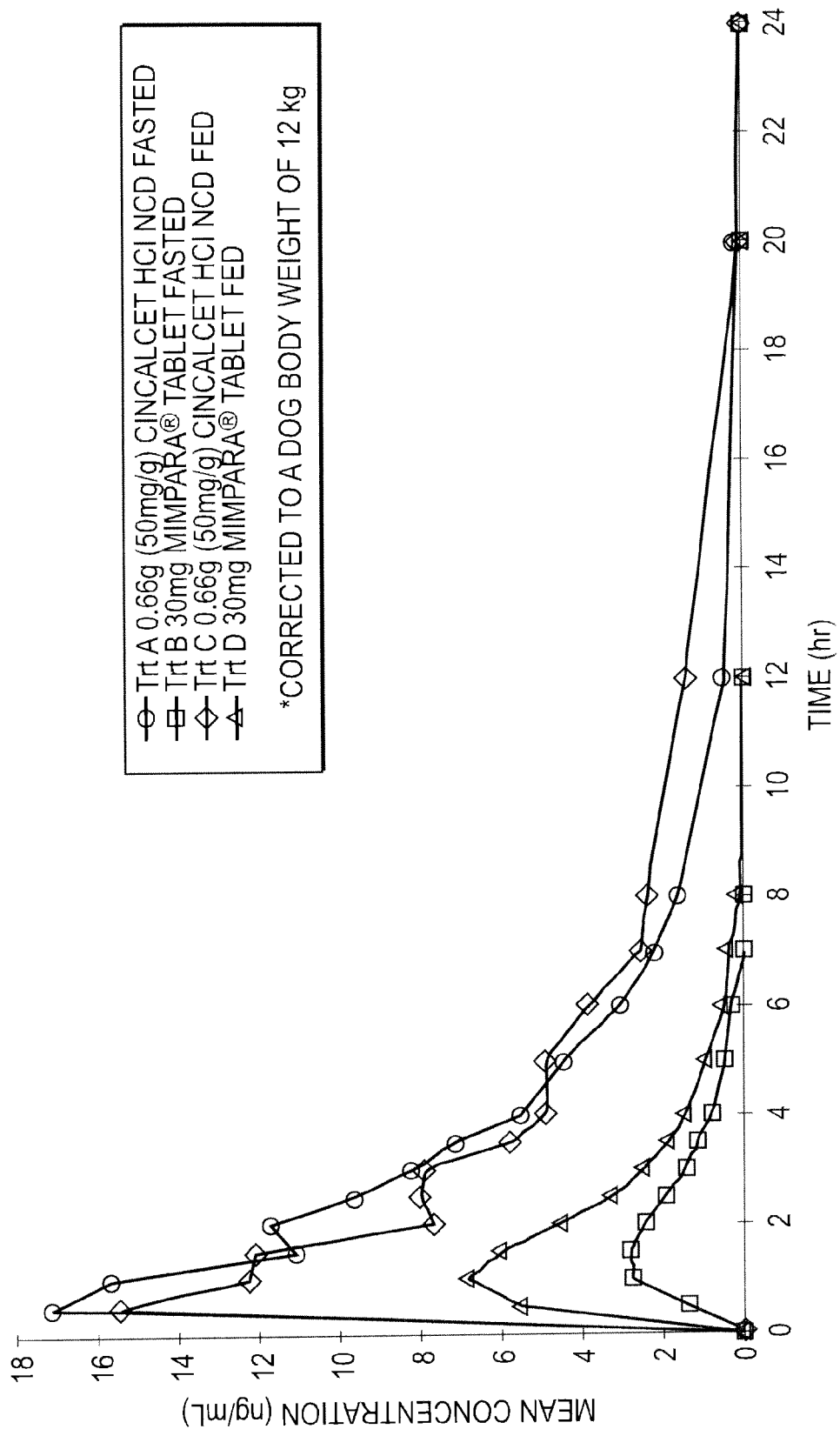

NANOPARTICULATE CINACALCET COMPOSITIONS

CROSS-REFERENCE TO RELATED APPLICATION

This application claims priority of U.S. Provisional Patent Application No. 61/346,331, filed on May 19, 2010, specifically incorporated by reference.

FIELD OF THE INVENTION

The present invention relates to nanoparticulate compositions of cinacalcet and methods of making and using such compositions. The compositions comprise cinacalcet particles having an effective average particle size of less than about 2000 nm. The invention further relates to controlled release cinacalcet compositions.

BACKGROUND OF THE INVENTION

A. Background Regarding Cinacalcet

Cinacalcet hydrochloride is a calcimimetic agent that increases the sensitivity of the calcium-sensing receptor to activation by extracellular calcium. It is sold as Sensipar® in the USA and Australia, and Mimpara® in Europe. Its empirical formula is $C_{22}H_{22}F_3N.HCl$ with a molecular weight of 393.9 g/mol (hydrochloride salt) and 357.4 g/mol (free base). It has one chiral center having an R-absolute configuration. The R-enantiomer is the more potent enantiomer and has been shown to be responsible for pharmacodynamic activity (Sensipar® prescribing information; www.sensipar.com/professional/pdf/sensipar_pi.pdf, accessed Jun. 11, 2008). The structural formula of cinacalcet hydrochloride is shown below:

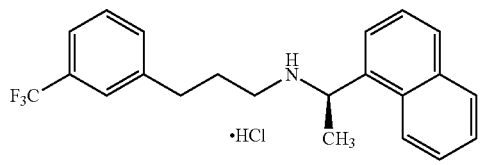 [SMILES: C[C@@H](NCCCc1cccc(C(F)(F)F)c1)c1cccc2ccccc12 ; Cl]

Cinacalcet HCl reduces iPTH, serum calcium, serum phosphorus, and the calcium-phosphorus product in patients with chronic kidney disease and secondary hyperparathyroidism who are receiving dialysis, and reduces elevated serum calcium associated with primary hyperparathyroidism and parathyroid carcinoma. Cinacalcet was approved in the US on 8 Mar. 2004 (NDA No. 021688) where it is sold under the tradename Sensipar® and in the European Union on 22 Oct. 2004 (MA EU/1/04/292/001-012) where it is sold as Mimpara®. Sensipar®/Mimpara® is indicated for the treatment of secondary hyperparathyroidism in patients with Chronic Kidney Disease on dialysis. Sensipar® is also indicated for the treatment of hypercalcemia in patients with parathyroid carcinoma. In January 2008, Kirin Pharma (now Kyowa Hakko Kirin) launched cinacalcet, as Regpara™, for the treatment of secondary hyperparathyroidism. In June 2008, cinacalcet was approved in the EU for the treatment of hypercalcemia in primary hyperparathyroidism.

In patients with secondary hyperparathyroidism and end-stage renal disease on dialysis, cinacalcet is to be administered orally starting at 30 mg, once daily. The dose should be titrated every 2 to 4 weeks up to 180 mg daily, to achieve a target PTH level. For patients with parathyroid carcinoma the recommended starting oral dose of Sensipar® is 30 mg twice daily. This should be titrated every 2 to 4 weeks through sequential doses of 30 mg twice daily, 60 mg twice daily, 90 mg twice daily and 90 mg three or four times daily as necessary to normalize serum calcium levels.

Cinacalcet is administered orally, and concomitant administration with food affects its bioavailability. Studies have confirmed this fact. Specifically, a study comparing the absorption of a single oral dose of cinacalcet HCl (Sensipar®/Mimpara® (90 mg) following (i) a high-fat, high-caloric meal, (ii) a low-fat, low-caloric meal, and a (iii) 10-hour fast, showed that the mean (90% confidence intervals) AUC[infinity] following high- and low-fat meals was increased by 68 (48 to 89) % and 50 (33 to 70) %, respectively, relative to fasting. The difference in mean $AUC_\infty$ between high- and low-fat meals was small [12 (9.9-26) %]. Moreover, the mean $t_{max}$ of cinacalcet was prolonged in fasting subjects (6 h) in relation to high-fat (4 h) and low-fat (3.5 h) fed subjects. The mean $t_{1/2[beta]}$ was similar between treatment conditions. See *American J. of Therapeutics*, 14:235-240 (May/June 2007). Thus, administration of cinacalcet with either high- or low-fat meals results in significant increases in exposure, relative to administration under fasting conditions. This change in exposure requires that the medication be taken with food or shortly after a meal. If a patient does not take their dose exactly as indicated sub-therapeutic levels of cinacalcet can occur. A recommendation that cinacalcet to be taken with food or shortly after a meal is included in the labeling information issued by the FDA and EMEA in respect of the Sensipar® and Mimpara® products respectively (see FDA 2004 label information and EMEA 2004 Summary of Product Characteristics, available on the relevant agency's website). In the case of the US product the most recent revision of the label information (19 Dec. 2008) maintains this recommendation. The absolute bioavailability of cinacalcet in fasted subjects has been estimated at 20-25% (EMEA 2004 Summary of Product Characteristics for Mimpara®)

More generally, cinacalcet is used to treat hyperparathyroidism (elevated parathyroid hormone levels) Torres PU, "Cinacalcet HCl: a novel treatment for secondary hyperparathyroidism caused by chronic kidney disease". *Journal of renal nutrition: the official journal of the Council on Renal Nutrition of the National Kidney Foundation* 16 (3): 253-8. (2006), and the symptoms thereof. Hyperparathyroidism is overactivity of the parathyroid glands resulting in excess production of parathyroid hormone (PTH). Parathyroid hormone regulates calcium and phosphate levels and helps to maintain these levels. Overactivity of one or more of the parathyroid glands causes high calcium levels (hypercalcemia) and low levels of phosphate in the blood. Hyperparathyroidism may be a consequence of parathyroid tumors and chronic renal failure.

Cinacalcet HCl is a white to off-white, crystalline solid soluble in methanol or 95% ethanol, but only slightly soluble in water. As such, the dissolution rate and bioavailability of known cinacalcet formulations are not optimal. The effectiveness of cinacalcet may be enhanced if it could be formulated to be taken without food, thus decreasing the likelihood of patient compliance problems. Furthermore a formulation that enhances the bioavailability of cinacalcet would facilitate reduction of the dosage strength with the possibility of achieving a better safety profile.

U.S. Pat. No. 6,011,068, U.S. Pat. No. 6,031,003, U.S. Pat. No. 6,211,244 and U.S. Pat. No. 6,313,146 are listed in respect of Sensipar® in the FDA's list of Approved Drug Products with Therapeutic Equivalence Evaluations (otherwise known as the "Orange Book"; see www.fda.gov/cder/ob/default.htm—accessed 5 May, 2009). Collectively these patents cover the cinacalcet compound per se, pharmaceutical compositions comprising cinacalcet and various uses including those listed in the Orange Book, namely: reducing parathyroid hormone level; modulating parathyroid hormone secretion; treating hyperparathyroidism; and reducing serum ionized calcium level.

B. Background Regarding Nanoparticulate Active Agent Compositions

Nanoparticulate active agent compositions, first described in U.S. Pat. No. 5,145,684 ("the '684 patent"), are particles comprising a poorly soluble therapeutic or diagnostic agent having adsorbed onto, or associated with, the surface thereof a non-crosslinked surface stabilizer. The '684 patent does not describe nanoparticulate compositions of cinacalcet.

Methods of making nanoparticulate active agent compositions are described in, for example, U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles." These do not describe nanoparticulate compositions of cinacalcet.

Nanoparticulate active agent compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,352,459 for "Use of Purified Surface Modifiers to Prevent Particle Aggregation During Sterilization;" U.S. Pat. No. 5,429,824 for "Use of Tyloxapol as a Nanoparticulate Stabilizer;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,622,938 for "Sugar Based Surfactant for Nanocrystals;" U.S. Pat. No. 5,718,388 for "Continuous Method of Grinding Pharmaceutical Substances;" U.S. Pat. No. 5,834,025 for "Reduction of Intravenously Administered Nanoparticulate Formulation Induced Adverse Physiological Reactions;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form;" U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive Nanoparticulate Compositions Having Cationic Surface Stabilizers;" U.S. Pat. No. 6,431,478 for "Small Scale Mill;" U.S. Pat. No. 6,432,381 for "Methods for Targeting Drug Delivery to the Upper and/or Lower Gastrointestinal Tract;" U.S. Pat. No. 6,592,903 for "Nanoparticulate Dispersions Comprising a Synergistic Combination of a Polymeric Surface Stabilizer and Dioctyl Sodium Sulfosuccinate," U.S. Pat. No. 6,582,285 for "Apparatus for sanitary wet milling;" U.S. Pat. No. 6,742,734 for "System and Method for Milling Materials;" U.S. Pat. No. 6,745,962 for "Small Scale Mill and Method Thereof;" U.S. Pat. No. 6,811,767 for "Liquid droplet aerosols of nanoparticulate drugs;" U.S. Pat. No. 6,908,626 for "Compositions having a combination of immediate release and controlled release characteristics;" U.S. Pat. No. 6,969,529 for "Nanoparticulate compositions comprising copolymers of vinyl pyrrolidone and vinyl acetate as surface stabilizers;" U.S. Pat. No. 6,976,647 for "System and Method for Milling Materials;" U.S. Pat. No. 6,991,191 for "Method of Using a Small Scale Mill;" U.S. Pat. No. 7,198,795 for "In vitro methods for evaluating the in vivo effectiveness of dosage forms of microparticulate of nanoparticulate active agent compositions;" U.S. Pat. No. 7,244,451 for "Methods of making nanoparticulate drug compositions comprising copolymers of vinyl pyrrolidone and vinyl acetate as surface stabilizers"; U.S. Pat. No. 7,288,267 for "Bioadhesive nanoparticulate compositions having cationic surface stabilizers"; U.S. Pat. No. 7,320,802 for "Methods of treatment using nanoparticulate fenofibrate compositions;" U.S. Pat. No. 7,390,505 for "Nanoparticulate topiramate formulations;" U.S. Pat. No. 7,459,283 for "Nanoparticulate compositions having lysozyme as a surface stabilizer;" U.S. Pat. No. 7,521,068 for "Dry powder aerosols of nanoparticulate drugs;" U.S. Pat. No. 7,695,739 for "In vitro methods for evaluating the in vivo effectiveness of dosage forms of microparticulate or nanoparticulate active agent compositions;" U.S. Pat. No. 7,713,551 for "Gel stabilized nanoparticulate active agent compositions;" U.S. Pat. No. 7,763,278 for "Nanoparticulate polycosanol formulations and novel polycosanol combinations;" U.S. Pat. No. RE41,884 for "Reduction of intravenously administered nanoparticulate-formulation-induced adverse physiological reactions;" U.S. Pat. No. 7,825,087 for "Nanoparticulate and controlled release compositions comprising cyclosporine;" U.S. Pat. No. 7,842,232 for "Sterilization of dispersions of nanoparticulate active agents with gamma radiation;" U.S. Pat. No. 7,850,995 for "Bioadhesive nanoparticulate compositions having cationic surface stabilizers;" U.S. Pat. No. 7,879,360 for "Nanoparticulate compositions having a peptide as a surface stabilizer;" U.S. Pat. No. 7,910,577 for "Injectable nanoparticulate olanzapine formulations;" U.S. Pat. No. 7,927,627 for "Nanoparticulate fibrate formulations;" and U.S. Pat. No. 7,931,917 for "Nanoparticulate fibrate formulations," all of which are specifically incorporated by reference. These patents do not describe nanoparticulate compositions of cinacalcet.

In addition, U.S. Patent Publication Nos. 20080152585 for "Low viscosity liquid dosage forms"; 20080124393 for "Controlled release nanoparticulate compositions"; 20080025807 for "System and Method for Milling Materials"; 20080003295 for "Bioadhesive nanoparticulate compositions having cationic surface stabilizers"; 20070141159 for "Methods of Making Nanoparticulate Compositions Comprising Copolymers of Vinyl Pyrrolidone and Vinyl Acetate as Surface Stabilizers"; 20070110776 for "In vitro methods for evaluating the in vivo effectiveness of dosage forms of microparticulate or nanoparticulate active agent compositions;" 20020012675 A1 for "Controlled Release Nanoparticulate Compositions," 20040195413 A1, for "Compositions and method for milling materials," 20040173696 A1 for "Milling microgram quantities of nanoparticulate candidate compounds," 20020012675 A1 for "Controlled Release Nanoparticulate Compositions;" 20050238725 for "Nanoparticulate compositions having a peptide as a surface stabilizer;" 20050147664 for "Compositions comprising antibodies and methods of using the same for targeting nanoparticulate active agent delivery;" 20050031691 for "Gel stabilized nanoparticulate active agent compositions;" 20040258757 for "Liquid dosage compositions of stable nanoparticulate active agents;" 20040195413 for "Compositions and method for milling materials;" 20040156895 for "Solid dosage forms comprising pullulan;" 20040105889 for "Low viscosity liquid dosage forms;" 20040105778 for "Gamma irradiation of solid nanoparticulate active agents;" 20040015134 for "Drug delivery systems and methods;" 20030215502 for "Fast dissolving dosage forms having reduced friability;" 20030185869 for "Nanoparticulate compositions having lysozyme as a surface stabilizer;" 20030137067 for "Compositions having a combination of immediate release and controlled release characteristics;" 20030108616 for "Nanoparticulate compositions comprising copolymers of vinyl pyrrolidone and vinyl acetate as surface stabilizers;" 20030087308 for "Method for high through put screening using a small scale mill or microfluidics;" 20030023203 for "Drug delivery systems & methods;" 20020179758 for "System and method for milling materials; 20010053664 for "Apparatus for sanitary wet milling," 20110064803 for "Nanoparticulate and controlled release compositions comprising vitamin k2;" 20110027371 for "Nanoparticulate statin formulations and novel statin combinations;" 20110008435 for "Nanoparticulate and Controlled Release Compositions Comprising Aryl-Heterocyclic Compounds;" 20100316725 for "Reduction of flake-like aggregation in nanoparticulate active agent compositions;" 20100260859 "Controlled-release clozapine compositions;" 20100260858 for "Drug delivery composition;" 20100247636 for "Nanoparticulate and controlled release compositions comprising nilvadipine;" 20100221327 for "Nanoparticulate azelnidipine formulations;" 20100028439 for "Nanoparticulate stabilized anti-hypertensive compositions;" 20090304801 for "Aerosol and injectable formulations of nanoparticulate benzodiazepine;" 20090297596 for "Nanoparticulate and Controlled Release Compositions Comprising a Platelet Aggregation Inhibitor;" 20090291142 for "Nanoparticulate bicalutamide formulations;" 20090269400 for "Nanoparticulate and Controlled Release Compositions Comprising a Cephalosporin;" 20090252807 for "Nanoparticulate and Controlled Release Compositions Comprising Prostaglandin Derivatives;" 20090238884 for "Compositions for site-specific delivery of imatinib and methods of use;" 20090155331 for "Injectable nanoparticulate olanzapine formulations;" 20090074873 for "Nanoparticulate beclomethasone dipropionate compositions;" 20090035366 for "Nanoparticulate benzothiophene formulations;" 20080317843 for "Nanoparticulate formulations of modafinil;" 20080279929 for "Nanoparticulate and Controlled Release Compositions Comprising Cefditoren;" 20080254114 for "Controlled Release Compositions Comprising Heterocyclic Amide Derivative Nanoparticles;" 20080248123 for "Nanoparticulate anticonvulsant and immunosuppressive compositions;" 20080226734 for "Combination of a narcotic and non-narcotic analgesic;" 20080220074 for "Gamma radiation sterilized nanoparticulate docetaxel compositions and methods of making same;" 20080213378 for "Nanoparticulate statin formulations and novel statin combinations;" 20080213374 for "Nanoparticulate sorafenib formulations;" and 20080171091 for "Nanoparticulate compositions of immunosuppressive agents," describe nanoparticulate active agent compositions and are specifically incorporated by reference. These patent application publications do not describe nanoparticulate compositions of cinacalcet.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;". These are also specifically incorporated herein by reference. These patents do not describe nanoparticulate compositions of cinacalcet.

The present invention relates to nanoparticulate cinacalcet compositions, such as nanoparticulate cinacalcet HCl, which addresses the needs described above by providing nanoparticulate cinacalcet compositions which overcome the shortcomings of known non-nanoparticulate cinacalcet formulations.

SUMMARY OF THE INVENTION

The present invention relates to stable nanoparticulate compositions comprising cinacalcet, or a pharmaceutically acceptable salt thereof, and at least one surface stabilizer. In one embodiment, the composition comprises cinacalcet HCl as the active agent. The surface stabilizer is associated with the surface of the cinacalcet particles, for example, the surface stabilizer may be adsorbed onto the surface of the cinacalcet particle. The cinacalcet nanoparticles have good stability and have an effective average particle size of less than about 2000 nm. The nanoparticulate cinacalcet compositions of the invention may further comprise one or more pharmaceutically acceptable excipients, carriers and the like.

The compositions of the invention show surprisingly enhanced bioavailability, and a reduced "food effect" as compared to non-nanoparticulate cinacalcet compositions. The compositions exhibit substantially similar oral bioavailability in fed and fasted subjects. Without wishing to be limited by theory, it is thought that reducing the particle size to less than about 2000 nm increases the rate of dissolution of the drug particles leading to these improved performance characteristics.

The compositions may include cinacalcet particles which are in a crystalline phase, an amorphous phase, a semi-crystalline phase, or mixtures thereof.

The compositions may include one or more surface stabilizers. For example, the compositions may include at least one primary and at least one secondary surface stabilizer. Exemplary surface stabilizers include, but are not limited to nonionic surface stabilizers, ionic surface stabilizers, anionic surface stabilizers, cationic surface stabilizers, zwitterionic surface stabilizers and combinations thereof.

The invention also relates to compositions comprising nanoparticulate cinacalcet or a salt thereof, at least one surface stabilizer, and optionally one or more pharmaceutically acceptable excipients, carriers, and optionally one or more active agents useful for the treatment of cancers such as leukemias, myeloproliferative diseases and related disorders, or a combination thereof.

The compositions of the invention comprising cinacalcet or a pharmaceutically acceptable salt thereof, exhibit improved pharmacokinetic profiles as compared to known non-nanoparticulate cinacalcet compositions (i.e. cinacalcet compositions having an effective average particle size of greater than 2000 nm). For example, the $C_{max}$ and/or AUC of the nanoparticulate cinacalcet compositions can be greater than the $C_{max}$ and/or AUC for known non-nanoparticulate cinacalcet compositions administered at the same dosage. In addition, the $T_{max}$ of the nanoparticulate cinacalcet can be lower than that obtained for a known non-nanoparticulate cinacalcet compositions, administered at the same dosage. In addition, combinations of an improved $C_{max}$, AUC and $T_{max}$ profile can be exhibited by the nanoparticulate cinacalcet compositions of the invention, as compared to known non-nanoparticulate cinacalcet compositions. In further embodiments, the nanoparticulate cinacalcet compositions may result in minimal different absorption levels when administered under fed as compared to fasting conditions.

In some embodiments, the nanoparticulate cinacalcet compositions exhibit improved bioavailability as compared to known non-nanoparticulate cinacalcet compositions having an effective average particle size of greater than 2000 nm.

In some embodiments of the invention, when the nanoparticulate cinacalcet compositions of the invention are formulated into a solid dosage form, upon administration to a mammal, the solid dosage form of a nanoparticulate cinacalcet compositions preferably redisperses such that the redispersed cinacalcet particles have an effective average particle size of less than about 2 microns. In so doing the advantages associated with the nanoparticulate cinacalcet (with an effective average particle size of less than about 2000 nm) are retained.

The invention also relates to methods of making nanoparticulate cinacalcet compositions, or salt thereof. In some embodiments, the methods include contacting cinacalcet particles with at least one surface stabilizer for a time and under conditions sufficient to provide a nanoparticulate cinacalcet composition having an effective average particle size of less than about 2000 nm. A suitable surface stabilizer can be added to a nanoparticulate cinacalcet composition either before, during, or after particle size reduction. Any suitable means can be used to reduce the particle size of cinacalcet, including, but not limited to, milling, microfluidization, precipitation, homogenization and the like.

The invention also relates to the use of nanoparticulate cinacalcet compositions in the treatment of various conditions and methods of treatment using said compositions. In some methods, a composition comprising a nanoparticulate cinacalcet or salt thereof, having an effective average particle size of less than about 2000 nm, and at least one surface stabilizer, may be administered to a subject. By way of example, but not by way of limitation, the composition may be administered to treat the effects of hyperparathyroidism, including treatment of secondary hyperparathyroidism in patients with Chronic Kidney Disease on dialysis and hypercalcemia in patients with parathyroid carcinoma. Other methods of treatment using the nanoparticulate cinacalcet compositions of the invention will be readily apparent to those of skill in the art.

In a further embodiment the invention provides a controlled release composition comprising nanoparticulate cinacalcet, as previously described. The controlled release composition may comprise a tablet coated with a controlled release coating, a controlled release matrix tablet or a controlled release multiparticulate dosage form.

Both the foregoing summary of the invention and the following brief description of the drawings and the detailed description of the invention are exemplary and explanatory and are intended to provide further details of the invention as claimed. Other objects, advantages, and novel features will be readily apparent to those skilled in the art from the following detailed description of the invention.

BRIEF DESCRIPTION OF THE DRAWINGS

The FIGURE shows the profile of mean cinacalcet plasma concentration over time, in dogs (corrected to a body weight of 12 kg), for each of four different treatments. A: nanoparticulate cinacalcet in fasted dogs; B: Mimpara® treatment in fasted dogs; C: nanoparticulate cinacalcet in fed dogs; D: Mimpara® treatment in fed dogs.

DETAILED DESCRIPTION OF THE INVENTION

The present invention is directed to compositions comprising nanoparticulate cinacalcet, or a pharmaceutically acceptable salt thereof. The compositions comprise nanoparticulate cinacalcet, or a salt thereof, and at least one surface stabilizer, which may be adsorbed onto or otherwise associated with the surface of the drug.

Generally, the cinacalcet particles have an effective average particle size of less than about 2000 nm. As detailed below, advantages of the nanoparticulate cinacalcet compositions as compared to known non-nanoparticulate (having an effective average particle size of greater than 2000 nm) cinacalcet formulations can include, but are not necessarily limited to: (1) smaller tablet or other solid dosage form size; (2) smaller doses of cinacalcet required to obtain the same pharmacological effect; (3) increased bioavailability; (4) improved pharmacokinetic profiles; (5) substantially similar pharmacokinetic profiles when administered in the fed versus the fasted state; (6) bioequivalency when administered in the fed versus the fasted state; (7) increased rate of absorption of the nanoparticulate cinacalcet compositions; (8) an increased rate of dissolution; and (9) the possibility that the compositions can be used in conjunction with other active agents.

As described above, one of the problems present with known micronized (non-nanoparticulate) cinacalcet compositions (such as Sensipar® or Mimpara®) is that absorption of the drug (AUC) can differ by almost 70% when the drug is given under fed as compared to fasting conditions. This is highly undesirable, as it is generally recognized at least about ⅓ of all patients have poor compliance regarding consuming drugs per the labeling instructions. This means that for drugs having a wide variability in absorption when administered under fed as compared to fasting conditions, a large patient population does not receive a therapeutically desirable dosage. The present invention overcomes this problem as it was surprisingly discovered that nanoparticulate cinacalcet compositions according to the invention have minimal, if any, differences in absorption when the compositions are administered under fed as compared to fasting conditions. This discovery was surprising, as formulation of an active agent into a nanoparticulate composition does not always correlate with reduction or elimination of fed/fasted variability i.e. the impact, if any, observed when active ingredients exhibiting a food effect are formulated in a nanoparticulate composition varies from drug to drug in a manner which can not be readily predicted in advance.

Nanoparticulate cinacalcet compositions may result in reduced or eliminated side effects. Exemplary side effects include, but are not limited to; upset stomach; vomiting; diarrhea; dizziness; weakness; chest pain; burning, tingling, or unusual feelings of the lips, tongue, fingers, or feet; muscle aches or cramps; sudden tightening of the muscles in the hands, feet, face, or throat; seizures; and infection of dialysis access (surgically created blood vessel where blood leaves and enters the body during dialysis). According to the December, 2008 revision of label information issued by the FDA, postmarketing experience with Sensipar® identified rash, hypersensitivity, diarrhea and myalgia as adverse effects. Furthermore, isolated cases of hypotension, worsening heart failure and/or arrhythmia have been reported in Sensipar® treated patients with impaired cardiac function. It is noted that "[b]ecause these reactions arte reported voluntarily from a population of uncertain size, it is not always possible to reliably estimate their frequency or establish a causal relationship to drug exposure." However, in general terms reducing the amount of drug to which patients are exposed, while at the same time maintaining efficacious levels, may help to reduce adverse effects and improve the safety profile of the product. Because nanoparticulate cinacalcet compositions can have a greater bioavailability, the nanoparticulate cinacalcet compositions can enable the use of a smaller dosage as compared to known non-nanoparticulate cinacalcet compositions, thereby facilitating a reduction in side effects.

The present invention also includes compositions further comprising one or more non-toxic physiologically acceptable carriers, adjuvants, or vehicles, collectively referred to as carriers. The compositions can be formulated for administration via any pharmaceutically acceptable means, including but not limited to, parental injection (e.g., intravenous, intramuscular, or subcutaneous), oral administration in solid, liquid, or aerosol form, bioadhesive, vaginal, nasal, rectal, ocular, local (powders, ointments, or drops), buccal, intracisternal, intraperitoneal, or topical administrations, and the like. The small size of the cinacalcet particles (i.e. less than 2000 nm) makes the composition of the invention particularly advantageous for parenteral formulations.

Oral administration is typically preferred, because of ease of administration and greater compliance. Oral dosage forms may be solid or liquid (e.g. a syrup). Exemplary solid oral dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

There is no universally accepted definition of terms such as "nanotechnology", "nanoparticle" or "nanoparticulate" (see for example: "*Nanotechnology*" A Report of the US Food and Drug Administration Nanotechnology Task Force, 25 Jul. 2007: "while one definition for "nanotechnology", "nanoscale material", or a related tem or concept may offer meaningful guidance in one context, that definition may be too narrow or broad to be of use in another" (p. 6-7) and "[i]dentifying precisely what qualifies as a nanoscale material is difficult and currently a subject of substantial discussion in the scientific, regulatory, and standards communities" (p. 8)). Nanoparticulate active agents as defined herein have an effective average particle size of less than about 2000 nm. By way of contrast, the term "non-nanoparticulate active agent" shall mean an active agent which is solubilized or which has an effective average particle size of greater than 2000 nm.

The term "cinacalcet", as used herein, expressly includes cinacalcet salts and encompasses different crystal forms (polymorphs) and hydrates. It also includes racemic or substantially optically pure forms of the foregoing The terms "drug" or "active agent," when used herein, typically refers to cinacalcet but may, if clearly indicated by its context, refer to another drug.

The term "effective average particle size," as used herein, means that at least about 50% of the nanoparticulate cinacalcet particles have a size of less than about 2000 nm (by weight or by other suitable measurement, such as by volume, number, etc.), when measured by, for example, sedimentation flow fractionation, photon correlation spectroscopy, light scattering, disk centrifugation, and other techniques known to those of skill in the art.

The term "one," "a," or "an," as used herein, is not limited to singular forms but also encompasses the plural equivalent.

The phrase "poorly water soluble drugs" as used herein refers to those drugs that have a solubility in water of less than about 30 mg/ml, less than about 20 mg/ml, less than about 10 mg/ml, or less than about 1 mg/ml.

As used herein with reference to stable nanoparticulate cinacalcet particles, "stable" connotes, but is not limited to one or more of the following parameters: (1) the particles do not appreciably flocculate or agglomerate due to interparticle attractive forces or otherwise significantly increase in particle size over time; (2) the physical structure of the particles is not altered over time, such as by conversion from an amorphous phase to a crystalline phase; (3) the particles are chemically stable; and/or (4) where the cinacalcet has not been subject to a heating step at or above the melting point of the cinacalcet particles in the preparation of the nanoparticles of the present invention.

As used herein, the phrase "therapeutically effective amount" shall mean that drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

The terms "treatment," "therapy," "therapeutic" and the like, as used herein, encompass any course of medical intervention aimed at a pathologic condition, and includes not only permanent cure of a disease, but prevention of disease, control or even steps taken to mitigate a disease or disease symptoms.

A. Characteristics of the Nanoparticulate Cinacalcet Compositions of the Invention 1. Increased Bioavailability The compositions of the invention comprising nanoparticulate cinacalcet can exhibit increased bioavailability as compared to the same non-nanoparticulate cinacalcet (in other words compared to a composition wherein the cinacalcet component is present at a particle size greater than 2000 nm). Moreover, the compositions of the invention are expected to require smaller doses, and smaller tablet or other solid dosage form size as compared to prior known non-nanoparticulate formulations of the same cinacalcet to achieve the same pharmacological effect. The increased bioavailability is significant because it means that the nanoparticulate cinacalcet dosage form will likely exhibit significantly greater drug absorption compared to the same amount of cinacalcet presented in the form of particles greater than about 2000 nm.

2. Improved Pharmacokinetic Profiles

The invention also enables production of compositions comprising nanoparticulate cinacalcet having a desirable pharmacokinetic (PK) profile when administered to mammalian subjects. Standard PK parameters routinely used to assess the behavior of a dosage form in vivo (in other words when administered to an animal or human subject) include $C_{max}$ (peak concentration of drug in blood plasma), $T_{max}$ (the time at which peak drug concentration is achieved) and AUC (the area under the plasma concentration vs time curve). Methods for determining and assessing these parameters are well known in the art. The desirable pharmacokinetic profile of the compositions comprising nanoparticulate cinacalcet may comprise but is not limited to: (1) a $C_{max}$ for a nanoparticulate cinacalcet when assayed in the plasma of a mammalian subject following administration, that is preferably greater than the $C_{max}$ for a non-nanoparticulate cinacalcet, administered at the same dosage; and/or (2) an AUC for nanoparticulate cinacalcet when assayed in the plasma of a mammalian subject following administration, that is preferably greater than the AUC for a non-nanoparticulate cinacalcet, administered at the same dosage; and/or (3) a $T_{max}$ for nanoparticulate cinacalcet when assayed in the plasma of a mammalian subject following administration, that is preferably less than the $T_{max}$ for a non-nanoparticulate formulation of the same drug administered at the same dosage. Preferably the composition exhibits a PK profile having a combination of two or more of the features (1), (2) and (3) in the preceding sentence. The desirable pharmacokinetic profile, as used herein, is the pharmacokinetic profile measured after the initial dose.

In one embodiment, a composition comprising nanoparticulate cinacalcet exhibits, in comparative pharmacokinetic testing with a non-nanoparticulate formulation of the same drug, administered at the same dosage, a $T_{max}$ not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the $T_{max}$ exhibited by the non-nanoparticulate cinacalcet formulation.

In another embodiment, the composition comprising nanoparticulate cinacalcet exhibits in comparative pharmacokinetic testing with a non-nanoparticulate formulation of the same drug, administered at the same dosage, a $C_{max}$ which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the $C_{max}$ exhibited by the non-nanoparticulate formulation.

In yet another embodiment, the composition comprising nanoparticulate cinacalcet exhibits in comparative pharmacokinetic testing with a non-nanoparticulate formulation of the same drug, administered at the same dosage, an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the non-nanoparticulate formulation.

In one embodiment of the invention, the $T_{max}$ of nanoparticulate cinacalcet when assayed in the plasma of the mammalian subject is less than about 6 hours. In other embodiments of the invention, the $T_{max}$ of the cinacalcet is less than about 5.5 hours, less than about 5 hours, less than about 4.5 hours, less than about 4 hours, less than about 3.5 hours, less than about 3 hours, less than about 2.5 hours, less than about 2 hours, less than about 1.5 hours less than about 1 hour, less than about 45 minutes, or less than about 30 minutes after administration.

The desirable pharmacokinetic profile, as used herein, is the pharmacokinetic profile measured after the initial dose of nanoparticulate cinacalcet. The compositions can be formulated in any way as described herein and as known to those of skill in the art.

3. The Pharmacokinetic Profiles of the Nanoparticulate Cinacalcet Compositions of the Invention are not Affected by the Fed or Fasted State of the Subject Ingesting the Compositions The invention encompasses compositions comprising nanoparticulate cinacalcet wherein the pharmacokinetic profile of the drug is not substantially affected by the fed or fasted state of a subject ingesting the composition. In other words the composition does not produce significantly different absorption levels when administered under fed as compared to fasted conditions. This means that there is no substantial difference in the quantity of drug absorbed (AUC), the rate of drug absorption ($C_{max}$), or the length of time to $C_{max}(T_{max})$, when the nanoparticulate cinacalcet compositions are administered in the fed versus the fasted state.

The difference in absorption (AUC) or $C_{max}$ of the nanoparticulate cinacalcet compositions of the invention, when administered in the fed versus the fasted state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

The difference in $T_{max}$ of the nanoparticulate cinacalcet compositions of the invention, when administered in the fed versus the fasted state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

4. Bioequivalency of Nanoparticulate Cinacalcet Compositions of the Invention when Administered in the Fed Versus the Fasted State The invention also encompasses a composition comprising nanoparticulate cinacalcet in which administration of the composition to a subject in a fasted state is bioequivalent to administration of the composition to a subject in a fed state.

In the field of pharmaceutical development the term "bioequivalence" will be readily understood and appreciated by the person skilled in the art. Various regulatory authorities have strict criteria and tests for assessing whether or not two drug products are bioequivalent. These criteria and tests are commonly used throughout the pharmaceutical industry and the assessment of bioequivalence is recognized as a standard form of activity in drug development programs where the characteristics and performance of one product are being compared to those of another product. Indeed in seeking approval to market certain types of products (e.g. those evaluated under the FDA's "Abbreviated New Drug Application" procedure), it is a requirement that the follow-on product be shown to be bioequivalent to a reference product.

In one embodiment of the invention, the invention encompasses compositions comprising nanoparticulate cinacalcet wherein administration of the composition to a subject in a fasted state is bioequivalent to administration of the composition to a subject in a fed state, in particular as defined by $C_{max}$ and AUC guidelines given by the U.S. Food and Drug Administration and the corresponding European regulatory agency (EMEA). Under U.S. FDA and Europe's EMEA guidelines, two products or methods are bioequivalent if the 90% Confidence Intervals (CI) for AUC and $C_{max}$ are between 0.80 to 1.25 ($T_{max}$ measurements are not relevant to bioequivalence for regulatory purposes). (Europe's EMEA previously used a different standard, which required a 90% CI for AUC between 0.80 to 1.25 and a 90% CI for $C_{max}$ between 0.70 to 1.43). Methods for determining $C_{max}$ and AUC are well known in the art.

5. Dissolution Profiles of the Nanoparticulate Cinacalcet Compositions of the Invention When formulated into a solid dosage form, the compositions comprising nanoparticulate cinacalcet are proposed to have unexpectedly dramatic dissolution profiles. Rapid dissolution of an administered active agent is preferable, as faster dissolution generally leads to greater bioavailability and faster onset of action. To improve the dissolution profile and bioavailability of cinacalcet it would be useful to increase cinacalcet's dissolution so that it could attain a level close to 100% dissolution of the drug substance.

The nanoparticulate cinacalcet compositions of the invention, when formulated into a solid dosage form, preferably have a dissolution profile in which within about 5 minutes at least about 20% of the composition is dissolved. In other embodiments of the invention, at least about 30% or at least about 40% of the cinacalcet composition is dissolved within about 5 minutes. In yet other embodiments of the invention, preferably at least about 40%, at least about 50%, at least about 60%, at least about 70%, or at least about 80% of the cinacalcet composition is dissolved within about 10 minutes. Finally, in another embodiment of the invention, preferably at least about 70%, at least about 80%, at least about 90%, or at least about 100% of the cinacalcet composition is dissolved within 20 minutes.

Dissolution is preferably measured in a medium which is discriminating. A discriminating dissolution medium is one that will produce different dissolution curves for two products having different dissolution profiles in gastric juices; i.e., the dissolution medium is predictive of the in vivo dissolution of a composition. An exemplary dissolution medium is an aqueous medium containing the surfactant sodium lauryl sulfate at 0.025 M. Determination of the amount dissolved can be carried out by spectrophotometry. The rotating blade method (see for example European Pharmacopoeia, $6^{th}$ Edition, 2007) can be used to measure dissolution.

6. Redispersibility of the Nanoparticulate Cinacalcet Compositions of the Invention An additional feature of the compositions comprising nanoparticulate cinacalcet is that when the compositions are formulated into a solid dosage form, the compositions redisperse such that the effective average particle size of the redispersed nanoparticulate cinacalcet particles is less than about 2 microns. This is significant, as upon administration, if the nanoparticulate cinacalcet particles of the compositions of the present invention agglomerated or did not redisperse to a substantially nanoparticulate size, then the solid dosage form may lose the benefits afforded by formulating the cinacalcet into a nanoparticulate size.

This is because nanoparticulate active agent compositions benefit from the small particle size of the active agent. If the active agent does not disperse into the small particle sizes upon administration, then "clumps" or agglomerated active agent particles are formed, owing to the extremely high surface free energy of the nanoparticulate system and the thermodynamic driving force to achieve an overall reduction in free energy. With the formulation of such agglomerated particles, the bioavailability of the dosage form may fall well below that observed with the liquid dispersion form of the nanoparticulate active agent.

Moreover, solid dosage forms comprising nanoparticulate cinacalcet compositions of the invention exhibit dramatic redispersion of the nanoparticulate cinacalcet particles upon administration to a mammal, such as a human or animal, as demonstrated by reconstitution/redispersion in a biorelevant medium such that the effective average particle size of the redispersed cinacalcet particles is less than about 2 microns. Such biorelevant medium can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1M while fasted state intestinal fluid has an ionic strength of about 0.14. See e.g., Lindahl et al., "Characterization of Fluids from the Stomach and Proximal Jejunum in Men and Women," *Pharm. Res.*, 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 M, and NaCl solutions, ranging in concentration from about 0.001 to about 0.1 M, and mixtures thereof. For example, electrolyte solutions can be, but are not limited to, about 0.1 M HCl or less, about 0.01 M HCl or less, about 0.001 M HCl or less, about 0.1 M NaCl or less, about 0.01 M NaCl or less, about 0.001 M NaCl or less, and mixtures thereof. Of these electrolyte solutions, 0.01 M HCl and/or 0.1 M NaCl, are most representative of fasted human physiological conditions, owing to the pH and ionic strength conditions of the proximal gastrointestinal tract.

Electrolyte concentrations of 0.001 M HCl, 0.01 M HCl, and 0.1 M HCl correspond to pH 3, pH 2, and pH 1, respectively. Thus, a 0.01 M HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+sodium, potassium and calcium salts of chloride.

In other embodiments of the invention, the redispersed particles of nanoparticulate cinacalcet (redispersed in water, a biorelevant media, any suitable redispersion media or dispersed following administration to an animal or human subject), have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 950 nm, less than about 900 nm, less than about 850 nm, less than about 800 nm, less than about 750 nm, less than about 700 nm, less than about 650 nm, less than about, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100, less than about 75 nm, or less than about 50 nm, as measured by light-scattering methods, microscopy, or other appropriate methods. Apart from the methods referred to herein, other methods suitable for measuring effective average particle size are known to a person of ordinary skill in the art. Typical biorelevant media in which redispersibility can be determined include for example water, aqueous electrolyte solutions (e.g. salt solutions), buffers, aqueous acid or base media and the like.

Redispersibility can be tested using any suitable means known in the art.

7. Nanoparticulate Cinacalcet Compositions Used in Conjunction with Other Active Agents Compositions comprising nanoparticulate cinacalcet can additionally comprise one or more compounds. This is significant, as cinacalcet is used for treatment of patients with chronic kidney disease with secondary hyperparathyroidism, a population that commonly receives multiple concurrent medications. For example, because cinacalcet is prescribed for hyperparathyroidism secondary to dialysis associated with chronic kidney disease, a nanoparticulate cinacalcet formulation may also comprise bioavailable phosphorous. Cinacalcet can also be co-administered (in a single or multiple compositions) with transplant drugs, such as cyclosporine, tacrolimus, and sirolimus, as cinacalcet offers a novel therapeutic option to treat post-transplant hypercalcemia and hyperparathyroidism.

Cinacalcet is eliminated primarily via oxidative metabolism mediated, in part, through cytochrome P450 (CYP) 3A4. Inhibitors of CYP3A4 such as ketoconazole, erythromycin, and itraconazole, can significantly increase cinacalcet exposure. Thus, coadministration with such a compound can reduce the dose of cinacalcet required to obtain the desired pharmacological effect.

Other types of drugs that may be given with cinacalcet include anticoagulants (which may be given after transplant surgery), such as warfarin.

B. Nanoparticulate Cinacalcet Compositions

The compositions of the invention comprise nanoparticulate cinacalcet, or a pharmaceutically acceptable salt thereof. The cinacalcet salt may be an addition salt formed with a suitable organic or inorganic acid such as for example HCl, HBr, $H_2SO_4$, phosphoric acid, sulphamic acid, oxalic acid, lactic acid, malonic acid, tartaric acid, succinic acid, acetic acid, citric acid, methansulphonic acid, ethanesulphonic acid, benzesulphonic acid, p-toluenesulphonic acid and the like. The hydrochloride salt of cinacalcet is preferred. The cinacalcet may be present in racemic form or as a substantially optically pure enantiomer. The compositions preferably comprise the R-enantiomer given that it is the more potent enantiomer. Three polymorphs of cinacalcet, referred to as Forms I, II and III are known (see for example WO 2009/02427 Amgen, Inc). The present invention may be practiced with any single polymorph or a mixture thereof. Preferably the composition comprises cinacalcet in the form of a substantially pure single polymorph, which may be Form I, Form II or Form III. The invention provides compositions comprising nanoparticulate cinacalcet and at least one surface stabilizer. The at least one surface stabilizer is preferably adsorbed on, or otherwise associated with, the surface of the cinacalcet particles. Surface stabilizers may physically adhere on, or associate with, the surface of the cinacalcet particles, but ideally do not chemically react with the cinacalcet particles or itself. Individually adsorbed molecules of the surface stabilizer are essentially free of intermolecular cross-linkages.

The present invention also includes nanoparticulate cinacalcet compositions together with one or more non-toxic physiologically acceptable carriers, adjuvants, or vehicles, collectively referred to as carriers. The compositions can be formulated for any pharmaceutically acceptable method of administration, such as parenteral injection (e.g., intravenous, intramuscular, or subcutaneous), oral administration in solid, liquid, or aerosol form, vaginal, nasal, rectal, ocular, local (powders, ointments or drops), buccal, intracisternal, intraperitoneal, or topical administration, and the like. A preferred route of administration is oral administration.

Accordingly, compositions of the invention may be formulated: (a) for administration selected from the group consisting of oral, pulmonary, intravenous, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets and capsules; (c) into a dosage form selected from the group consisting of lyophilized formulations, fast melt formulations, controlled release formulations, delayed release formulations, extended release formulations, pulsatile release formulations, and mixed immediate release and controlled release formulations; and (d) combinations of (a), (b), and (c).

Controlled release (CR) formulations may take the form of tablets coated with a CR coating, CR matrix tablets or CR multiparticulates. For example such dosage forms are described in US 2002/0012675 ("Controlled release nanoparticulate compositions", Jain et al, filed 22 Jun. 1999), see paragraphs [0014] to [0023] in particular.

1. Nanoparticulate Cinacalcet Particles

The compositions of the invention comprise nanoparticulate cinacalcet or a salt thereof, in which the particles can be in a crystalline phase, semi-crystalline phase, amorphous phase, or a combination thereof.

2. Surface Stabilizers

The choice of a surface stabilizer for nanoparticulate cinacalcet is non-trivial. Accordingly, the present invention is directed to the surprising discovery that nanoparticulate cinacalcet compositions can be made.

The compositions of the invention comprise at least one surface stabilizer. However, combinations of more than one surface stabilizer have been found to be useful and can be used in the invention. Where a plurality of surface stablizers is used there may be a primary surface stabilizer that is present in greater concentration than the other (secondary) surface stabilizer(s). Preferably the composition will comprise a primary surface stabilizer and at least one secondary surface stabilizer. Useful surface stabilizers which can be employed in the invention include, but are not limited to, known organic and inorganic pharmaceutical excipients. Such excipients include various polymers, low molecular weight oligomers, natural products, and surfactants. Exemplary surface stabilizers include nonionic and ionic (e.g., anionic, cationic, and zwitterionic) stabilizers. Without wishing to be bound by any particular theory, it is believed that polymeric materials adhering to a particle surface can present a steric barrier preventing particle aggregation, while in the case of ionic stablizers the stabilizing action may be attributed to electrostatic interactions.

Representative examples of surface stabilizers include albumin, including but not limited to human serum albumin and bovine albumin, hydroxypropyl methylcellulose (now known as hypromellose), hydroxypropylcellulose, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tween® products such as e.g., Tween 20® and Tween 80® (ICI Specialty Chemicals)); polyethylene glycols (e.g., Carbowax 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hypromellose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as, Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-lOG® or Surfactant 10-G® (Olin Chemicals, Stamford, Conn.); Crodestas SL-40® (Croda, Inc.); and SA9OHCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-nonyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, and the like.

If desirable, the nanoparticulate cinacalcet compositions of the invention can be formulated to be phospholipid-free.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammonium bromide (PM-MTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quaternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$) dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), polyquaternium 10 (POLYQUAT 10™), tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, quaternized ammonium salt polymers (MIRAPOL™ and ALKAQUAT™, Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation*(Marcel Dekker, 1994); P. and D. Rubingh (Editor), *Cationic Surfactants: Physical Chemistry*(Marcel Dekker, 1991); and J. Richmond, *Cationic Surfactants. Organic Chemistry*, (Marcel Dekker, 1990).

Nonpolymeric surface stabilizers are any nonpolymeric compound, such benzalkonium chloride, a carbonium compound, a phosphonium compound, an oxonium compound, a halonium compound, a cationic organometallic compound, a quaternary phosphorous compound, a pyridinium compound, an anilinium compound, an ammonium compound, a hydroxylammonium compound, a primary ammonium compound, a secondary ammonium compound, a tertiary ammonium compound, and quaternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or
(xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The following surface stabilizers may be particularly useful in the practice of the present invention copolymers of vinylpyrrolidone and vinyl acetate or copovidone (e.g., Plasdone® S630, which is a random copolymer of vinyl acetate and vinyl pyrrolidone available from ISP Technologies, Inc (USA)); docusate sodium (DOSS); hydroxypropylcellulose (HPC, such as HPC-SL which has a viscosity of 2.0 to 2.9 mPa·s in aqueous 2% w/v solution at 20° C. (available from Nippon Soda Co Ltd, Japan); hydroxypropylmethylcellulose (HPMC, such as Pharmacoat® 603 available from Shin-Etsu Chemical Co Ltd, Japan); polysorbates or polyoxyethylene sorbitan fatty acid esters (such as those available under the Tween® tradename (ICI Speciality Chemicals, UK), such as Tween® 20 (polyoxyethylene 20 sorbitan monolaurate), Tween® 40 (polyoxyethylene 20 sorbitan palmitate) or Tween® 80 (polyoxyethylene 20 sorbitan monooleate)); block copolymers based on ethylene oxide and propylene oxide, also known as poloxamers (e.g., poloxamer 407 (*Lutrol® F127 available from BASF AG, Germany), Poloxamer 188 (Lutrol® F68 available from BASF AG) or Poloxamer 338 (Lutrol® F108 available from BASF AG) (*these poloxamer products are also available under the Pluronic brand name (from BASF)); a polyvinylpyrrolidone (PVP), such as those available from ISP Corp (New Jersey, USA) under the Plasdone® trade name, e.g. Plasdone® C29/32 (which is equivalent to BASF PVP K29/32), Plasdone® C-30, Plasdone® C17 (equivalent to BASF PVP K-17) and Plasdone® C12 (equivalent to povidone K12); deoxycholic acid sodium salt, sodium lauryl sulphate (SLS also known as sodium dodecyl sulphate or SDS), benzalkonium chloride (also known as alkyldimethylbenzylammonium chloride), lecithin, distearyl palmitate glyceryl or a combination thereof. Other preferred stabilizers include albumin, lysozyme, gelatin, macrogol 15 hydroxystearate (available for example from BASF AG under the trade name Solutol® 15), tyloxapol and polyethoxylated castor oil (available for example from BASF AG under the trade name Cremophor® EL).

The surface stabilizers are commercially available and/or can be prepared by techniques known in the art. Most of these surface stabilizers are known pharmaceutical excipients and are described in detail in the *Handbook of Pharmaceutical Excipients*, published jointly by the American Pharmaceutical Association and The Pharmaceutical Society of Great Britain (R. C. Rowe et al (ed.) $5^{th}$ Edition, The Pharmaceutical Press, 2006), specifically incorporated by reference.

3. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents include lactose monohydrate, lactose anhydrous, and various starches; examples of binding agents include various celluloses and cross-linked polyvinylpyrrolidone, microcrystalline cellulose, such as Avicel® PH101 and Avicel® PH102 (available from FMC Corp, Pennsylvania, USA), microcrystalline cellulose, and silicified microcrystalline cellulose (ProSolv SMCC™ available from J. Rettenmaier & Sohne GmbH & Co. KG Ltd, Germany).

Suitable lubricants, including agents that act on the flowability of the powder to be compressed, may include colloidal silicon dioxide, such as Aerosil® 200 (available from Evonik Industries AG, Germany), talc, stearic acid, magnesium stearate, calcium stearate, and silica gel.

Examples of sweeteners may include any natural or artificial sweetener, such as sucrose, xylitol, sodium saccharin, cyclamate, aspartame, and acesulfame. Examples of flavoring agents are Magnasweet® (trademark of MAFCO), bubble gum flavor, and fruit flavors, and the like.

Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21 (available from DMV Fonterra Excipients GmbH & Co KG, Germany); dibasic calcium phosphate such as Emcompress® (available from J. Rettenmaier & Sohne GmbH & Co. KG Ltd, Germany); mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents include effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

4. Nanoparticulate Cinacalcet Particle Size

The small size of nanoparticles imparts some interesting and useful properties. For example, due to thermal fluctuation and Brownian motion suspended particles having a solid density of 1300 kg/m$^3$ and a particle size of 1000 nm at 25° C. occurs at a speed of about 1700 nm/sec (calculated according to Einstein's fluctuation-dissipation theory). The settling velocity for particles of the same size in water at 25° C. is significantly lower, approximately 185 nm/sec. In other words the gravitational pull (represented by settling velocity) is less that the random motion of the nanoparticles. This means that particles of 1000 nm will not settle under gravitational force. Larger particles of the same density e.g. around 2.5 μm or greater the settling velocity is such that the particles will not remain suspended unless assisted (e.g. by dispersing them in a thickened, more viscous, medium) or may form loosely aggregated flocs (also known as a flocculated suspension) which need to be shaken before use to redisperse the particles. Particles produced by any manufacturing process will be not be perfectly unimodal, but will instead be characterized by a distribution of different particle sizes. Recognizing that the above calculations are a simplification of the phenomena observed in practice (because they are based on discrete particle size values rather than particle size distributions) an effective average particle size of about 2000 nm represents a reasonable threshold value where sedimentation of particles (i.e. settling velocity is greater than thermal motion) is likely to become a significant factor in the stability or otherwise of a suspension or dispersion. The consideration of particle size and settling velocity in drug delivery is discussed in various pharmaceutics texts, see for example "Nanoparticle Technology for Drug Delivery" R. B. Gupta & U. B. Kompella (eds.), 2006 Taylor & Francis Group, LLC; pages 4-5).

Drug particles less than 2000 nm in size may tend to aggregate or flocculate in the absence of some stabilization mechanism (illustrated for example in U.S. Pat. No. 5,145,684 Comparative Example A). Particles of the present invention comprise a surface stabilizer for this reason.

The observation of some increase in particle size over time is not necessarily representative of an unstable nanoparticulate system. The key concern is whether or not particle size growth and/or aggregation occurs to the extent that the performance of the composition is compromised in some way e.g. the composition would not have the required shelf-life, or particle growth would result in precipitation of drug particles in a liquid dosage form, or particle growth would compromise the safety of the product (say for example in an intravenous product). Some degree of particle growth over time may not be detrimental to the overall product characteristics and the extent to which particle growth may be acceptable can depend on the route of administration (e.g. uncontrollable particle growth in a composition intended for IV administration could present safety risks). Further processing of a nanoparticulate dispersion to produce a solid dosage form will tend to mitigate particle growth and aggregation due to the removal of the particles from the liquid phase.

The compositions of the invention comprise nanoparticulate cinacalcet particles having an effective average particle size of less than about 2000 nm (i.e., 2 microns), less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 990 nm, less than about 980 nm, less than about 970 nm, less than about 960 nm, less than about 950 nm, less than about 940 nm, less than about 930 nm, less than about 920 nm, less than about 910 nm, less than about 900 nm, less than about 890 nm, less than about 880 nm, less than about 870 nm, less than about 860 nm, less than about 850 nm, less than about 840 nm, less than about 830 nm, less than about 820 nm, less than about 810 nm, less than about 800 nm, less than about 790 nm, less than about 780 nm, less than about 770 nm, less than about 760 nm, less than about 750 nm, less than about 740 nm, less than about 730 nm, less than about 720 nm, less than about 710 nm, less than about 700 nm, less than about 690 nm, less than about 680 nm, less than about 670 nm, less than about 660 nm, less than about 650 nm, less than about 640 nm, less than about 630 nm, less than about 620 nm, less than about 610 nm, less than about 600 nm, less than about 590 nm, less than about 580 nm, less than about 570 nm, less than about 560 nm, less than about 550 nm, less than about 540 nm, less than about 530 nm, less than about 520 nm, less than about 510 nm, less than about 500 nm, less than about 490 nm, less than about 480 nm, less than about 470 nm, less than about 460 nm, less than about 450 nm, less than about 440 nm, less than about 430 nm, less than about 420 nm, less than about 410 nm, less than about 400 nm, less than about 390 nm, less than about 380 nm, less than about 370 nm, less than about 360 nm, less than about 350 nm, less than about 340 nm, less than about 330 nm, less than about 320 nm, less than about 310 nm, less than about 300 nm, less than about 290 nm, less than about 280 nm, less than about 270 nm, less than about 260 nm, less than about 250 nm, less than about 240 nm, less than about 230 nm, less than about 220 nm, less than about 210 nm, less than about 200 nm, less than about 190 nm, less than about 180 nm, less than about 170 nm, less than about 160 nm, less than about 150 nm, less than about 140 nm, less than about 130 nm, less than about 120 nm, less than about 110 nm, less than about 100, less than about 75 nm, or less than about 50 nm, as measured by light-scattering methods, microscopy, or other appropriate methods.

By "an effective average particle size of less than about 2000 nm" it is meant that at least 50% of the particles have a particle size less than the effective average, by weight (or by other suitable measurement techniques, such as by volume, number, etc.), i.e., less than about 2000 nm, 1900 nm, 1800 nm, etc., when measured by the above-noted techniques. In other embodiments of the invention, at least about 60%, at least about 70%, at least about 80% at least about 90%, at least about 95%, or at least about 99% of the cinacalcet particles have a particle size of less than the effective average, i.e., less than about 2000 nm, 1900 nm, 1800 nm, 1700 nm, etc.

In the present invention, the value for $D_{50}$ of a nanoparticulate cinacalcet composition is the particle size below which 50% of the cinacalcet particles fall, by weight (or by other suitable measurement techniques, such as by volume, number, etc.). Similarly, $D_{90}$ is the particle size below which 90% of the cinacalcet particles fall, by weight (or by other suitable measurement techniques, such as by volume, number, etc.).

Cinacalcet nanoparticles of less than about 200 nm are particularly advantageous for sterile formulations (e.g. for parenteral administration). Preferably such a formulation comprises cinacalcet particles having a $D_{95}$ less than about 200 nm in order to facilitate sterile filtration. Filtration can be an effective method of sterilizing homogeneous compositions when the membrane filter pore size is sufficiently small to remove bacteria (e.g. a pore size of the order to 200-220 nm or 0.20-0.22 μm). Sterile filtration techniques will be known to the person skilled in the art.

5. Concentration of Nanoparticulate Cinacalcet and Surface Stabilizers

The relative amounts of nanoparticulate cinacalcet and one or more surface stabilizers may vary. The optimal amount of the individual components can depend, for example, upon the particular form of cinacalcet (such as the specific salt) selected, the hydrophilic lipophilic balance (HLB), melting point, and the surface tension of water solutions of the stabilizer, etc.

In general the concentration of the cinacalcet in the nanoparticulate composition may be from about 99.5% to about 0.001%, from about 95% to about 0.1%, or from about 90% to about 0.5%, by weight, based on the total combined dry weight of the cinacalcet and at least one surface stabilizer, not including other excipients.

The concentration of the cinacalcet may be present in any amount sufficient to achieve therapeutically effective levels upon administration and may vary depending on the manner in which the composition is formulated. For example, when considering cinacalcet particles dispersed in a liquid medium, the cinacalcet may typically be present in an amount from about 0.5% to about 30% by weight (salt or free base equivalent) based on the total combined weight of the drug substance, stablizers, any added excipients and the weight of the dispersion medium. Or, in the case of a solid dosage form the cinacalcet may typically be present in an amount from about 0.1% to about 60% by weight, preferably 0.5% to 30% by weight, and more preferably 1.0% to 20% by weight (salt or free base equivalent) based on the total combined weight of the drug substance, stablizers, and excipients. (It will be appreciated that the calculation of a weight based concentration will depend on whether the concentration is determined as that of a particular cinacalcet salt or the free base equivalent.)

Any concentration of surface stabilizer(s) which is sufficient to form stable nanoparticles of cinacalcet may be used. For example, the concentration of the at least one surface stabilizer may be present from about 0.01% to about 99.99%, from about 5.0% to about 95.0%, or from about 10% to about 90.0%, by weight, based on the total combined dry weight of the cinacalcet and at least one surface stabilizer, not including other excipients. When considering dispersed cinacalcet particles, the at least one stabilizer may typically be present in an amount from about 0.01% to about 30% by weight based on the total combined weight of the drug substance, stablizers, any added excipients and the weight of the dispersion medium. Or, in the case of a solid dosage form the at least one stabilizer may typically be present in an amount from about 0.1% to about 30% by weight, preferably 0.5% to 20% by weight, and more preferably 1.0% to 10% by weight based on the total combined weight of the drug substance, stablizers, and excipients. When more than one surface stabilizer is utilized the stabilizer present in the greatest concentration is the primary stabilizer and the other stabilizers are secondary stabilizers. For example the composition may typically comprise a primary surface stabilizer in an amount from about 1.0% to about 20% w/w (by weight of the total composition (including any dispersion medium)) and one or more secondary surface stabilizers each present in an amount, less than that of the primary stabilizer, ranging from about 0.01% to about 5% w/w (by weight of the total composition (including any dispersion medium). The combination of a primary stabilizer with one or more secondary stablizers can be advantageous over the use of a single stabilizer. For example a plurality of stabilizers can be used to combine the steric and electrostatic stabilization effects of different types of surface stabilizer molecules.

6. Exemplary Nanoparticulate Cinacalcet Tablet Formulations

Several exemplary tablet formulations are given below. These examples are not intended to limit the claims in any respect, but rather to provide exemplary tablet formulations of cinacalcet which can be utilized in the methods of the invention. Such exemplary tablets may also include a coating agent.

TABLE 1

Exemplary Nanoparticulate Cinacalcet Tablet Formulation #1

| Component | g/Kg |
|---|---|
| Cinacalcet HCl | about 50 to about 500 |
| Hypromellose, USP | about 10 to about 70 |
| Docusate Sodium, USP | about 1 to about 10 |
| Sucrose, NF | about 100 to about 500 |
| Lactose Monohydrate, NF | about 50 to about 400 |
| Silicified Microcrystalline Cellulose | about 50 to about 300 |
| Crospovidone, NF | about 20 to about 300 |
| Magnesium Stearate, NF | about 0.5 to about 5 |

TABLE 2

Exemplary Nanoparticulate
Cinacalcet Tablet Formulation #2

| Component | g/Kg |
| --- | --- |
| Cinacalcet HCl | about 100 to about 300 |
| Hypromellose, USP | about 30 to about 50 |
| Docusate Sodium, USP | about 0.5 to about 10 |
| Sucrose, NF | about 100 to about 300 |
| Sodium Lauryl Sulfate, NF | about 1 to about 30 |
| Lactose Monohydrate, NF | about 100 to about 300 |
| Silicified Microcrystalline Cellulose | about 50 to about 200 |
| Crospovidone, NF | about 50 to about 200 |
| Magnesium Stearate, NF | about 0.5 to about 5 |

TABLE 3

Exemplary Nanoparticulate
Cinacalcet Tablet Formulation #3

| Component | g/Kg |
| --- | --- |
| Cinacalcet HCl | about 200 to about 225 |
| Hypromellose, USP | about 42 to about 46 |
| Docusate Sodium, USP | about 2 to about 6 |
| Sucrose, NF | about 200 to about 225 |
| Sodium Lauryl Sulfate, NF | about 12 to about 18 |
| Lactose Monohydrate, NF | about 200 to about 205 |
| Silicified Microcrystalline Cellulose | about 130 to about 135 |
| Crospovidone, NF | about 112 to about 118 |
| Magnesium Stearate, NF | about 0.5 to about 3 |

TABLE 4

Exemplary Nanoparticulate
Cinacalcet Tablet Formulation #4

| Component | g/Kg |
| --- | --- |
| Cinacalcet HCl | about 119 to about 224 |
| Hypromellose, USP | about 42 to about 46 |
| Docusate Sodium, USP | about 2 to about 6 |
| Sucrose, NF | about 119 to about 224 |
| Sodium Lauryl Sulfate, NF | about 12 to about 18 |
| Lactose Monohydrate, NF | about 119 to about 224 |
| Silicified Microcrystalline Cellulose | about 129 to about 134 |
| Crospovidone, NF | about 112 to about 118 |
| Magnesium Stearate, NF | about 0.5 to about 3 |

C. Methods of Making Nanoparticulate Cinacalcet Compositions

The present invention further relates to a method of making a nanoparticulate cinacalcet, or a salt thereof, composition comprising contacting particles of a cinacalcet with at least one surface stabilizer for a time and under conditions sufficient to provide a composition comprising particles of cinacalcet having an effective average particle size of less than about 2000 nm.

The compositions comprising nanoparticulate cinacalcet can be made using, for example, milling or attrition (including but not limited to wet milling), homogenization, precipitation, freezing, template emulsion techniques, supercritical fluid techniques, nanoelectrospray techniques, or any combination thereof. Exemplary methods of making nanoparticulate compositions are described in the '684 patent. Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

The resultant nanoparticulate cinacalcet compositions or dispersions can be utilized in any pharmaceutically acceptable dosage form, including but not limited to injectable dosage forms, liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

1. Milling to Obtain Nanoparticulate Cinacalcet Dispersions

Milling cinacalcet to obtain a nanoparticulate cinacalcet dispersion comprises dispersing the particles in a liquid dispersion medium in which the cinacalcet is poorly soluble, followed by applying mechanical means in the presence of grinding media to reduce the particle size of the cinacalcet to the desired effective average particle size. The dispersion medium can be, for example, water, safflower oil, ethanol, t-butanol, glycerin, polyethylene glycol (PEG), hexane, or glycol. In some embodiments, a preferred dispersion medium is water.

The cinacalcet particles can be reduced in size in the presence of at least one surface stabilizer. Alternatively, nanoparticulate cinacalcet can be contacted with one or more surface stabilizers after attrition. Other compounds, such as a diluent, can be added to the cinacalcet/surface stabilizer composition during the size reduction process. Dispersions can be manufactured continuously or in a batch mode.

The grinding media can comprise particles that are preferably substantially spherical in shape, e.g., beads, consisting essentially of polymeric or copolymeric resin. Alternatively, the grinding media can comprise a core having a coating of a polymeric or copolymeric resin adhered thereon.

In general, suitable polymeric or copolymeric resins are chemically and physically inert, substantially free of metals, solvent, and monomers, and of sufficient hardness and friability to enable them to avoid being chipped or crushed during grinding. Suitable polymeric or copolymeric resins include crosslinked polystyrenes, such as polystyrene crosslinked with divinylbenzene; styrene copolymers; polycarbonates; polyacetals, such as Delrin™ (E.I. du Pont de Nemours and Co.); vinyl chloride polymers and copolymers; polyurethanes; polyamides; poly(tetrafluoroethylenes), e.g., Teflon® (E.I. du Pont de Nemours and Co.), and other fluoropolymers; high density polyethylenes; polypropylenes; cellulose ethers and esters such as cellulose acetate; polyhydroxymethacrylate; polyhydroxyethyl acrylate; and silicone-containing polymers such as polysiloxanes and the like. The polymer can be biodegradable. Exemplary biodegradable polymers or copolymers include poly(lactides), poly(glycolide) copolymers of lactides and glycolide, polyanhydrides, poly(hydroxyethyl methacrylate), poly(imino carbonates), poly(N- acylhydroxyproline)esters, poly(N-palmitoyl hydroxyproline) esters, ethylene-vinyl acetate copolymers, poly(orthoesters), poly(caprolactones), and poly(phosphazenes). For biodegradable polymers or copolymers, contamination from the media itself advantageously can metabolize in vivo into biologically acceptable products that can be eliminated from the body.

The grinding media preferably ranges in size from about 0.01 to about 3 mm. For fine grinding, the grinding media is preferably from about 0.02 to about 2 mm, and more preferably from about 0.03 to about 1 mm in size.

The polymeric or copolymeric resin can have a density from about 0.8 to about 3.0 $g/cm^3$.

In a preferred grinding process the cinacalcet particles are made continuously. Such a method comprises continuously introducing a cinacalcet composition according to the invention into a milling chamber, contacting the cinacalcet composition according to the invention with grinding media while in the chamber to reduce the cinacalcet particle size of the composition according to the invention, and continuously removing the nanoparticulate cinacalcet composition from the milling chamber.

The grinding media is separated from the milled nanoparticulate cinacalcet composition according to the invention using known separation techniques, in a secondary process such as by simple filtration, sieving through a mesh filter or screen, and the like. Other separation techniques such as centrifugation may also be employed.

2. Precipitation to Obtain Nanoparticulate Cinacalcet Compositions

Another method of forming the desired nanoparticulate cinacalcet is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving cinacalcet in a suitable solvent; (2) adding the formulation from step (1) to a solution comprising at least one surface stabilizer; and (3) precipitating the formulation from step (2) using an appropriate non-solvent. The method can be followed by removal of any formed salt, if present, by dialysis or diafiltration and concentration of the dispersion by known means.

3. Homogenization to Obtain Nanoparticulate Cinacalcet Compositions

Exemplary homogenization methods of preparing active agent nanoparticulate compositions are described in U.S. Pat. No. 5,510,118, for "Process of Preparing Therapeutic Compositions Containing Nanoparticles." Such a method comprises dispersing cinacalcet particles in a liquid dispersion medium, followed by subjecting the dispersion to homogenization to reduce the particle size of cinacalcet to the desired effective average particle size. The cinacalcet particles can be reduced in size in the presence of at least one surface stabilizer. Alternatively, the cinacalcet particles can be contacted with one or more surface stabilizers either before or after attrition. Other compounds, such as a diluent, can be added to the cinacalcet/surface stabilizer composition either before, during, or after the cinacalcet particle size reduction process. Dispersions can be manufactured continuously or in a batch mode.

4. Cryogenic Methodologies to Obtain Nanoparticulate Cinacalcet Compositions

Another method of forming the desired nanoparticulate cinacalcet is by spray freezing into liquid (SFL). This technology comprises an organic or organoaqueous solution of cinacalcet with stabilizers, which is injected into a cryogenic liquid, such as liquid nitrogen. The droplets of cinacalcet solution freeze at a rate sufficient to minimize crystallization and particle growth, thus formulating nanostructured cinacalcet particles. Depending on the choice of solvent system and processing conditions, the nanoparticulate cinacalcet particles can have varying particle morphology. In the isolation step, the nitrogen and solvent are removed under conditions that avoid agglomeration or ripening of the cinacalcet particles.

As a complementary technology to SFL, ultra rapid freezing (URF) may also be used to created equivalent nanostructured cinacalcet particles with greatly enhanced surface area. URF comprises an organic or organoaqueous solution of cinacalcet with stabilizers onto a cryogenic substrate.

5. Emulsion Methodologies to Obtain Nanoparticulate Cinacalcet Compositions

Another method of forming the desired nanoparticulate cinacalcet is by template emulsion. Template emulsion creates nanostructured cinacalcet particles with controlled particle size distribution and rapid dissolution performance. The method comprises an oil-in-water emulsion that is prepared, then swelled with a non-aqueous solution comprising cinacalcet and stabilizers. The particle size distribution of cinacalcet is a direct result of the size of the emulsion droplets prior to loading with cinacalcet, a property which can be controlled and optimized in this process. Furthermore, through selected use of solvents and stabilizers, emulsion stability is achieved with no or suppressed Ostwald ripening. Subsequently, the solvent and water are removed, and the stabilized nanostructured cinacalcet particles are recovered. Various cinacalcet particle morphologies can be achieved by appropriate control of processing conditions.

6. Supercritical Fluid Methods of Making Cinacalcet Nanoparticles

Nanoparticulate cinacalcet compositions can also be made in methods utilizing supercritical fluids. In such a method cinacalcet is dissolved in a solution or vehicle which can also contain at least one surface stabilizer. The solution and a supercritical fluid are then co-introduced into a particle formation vessel. If a surface stabilizer was not previously added to the vehicle, it can be added to the particle formation vessel The temperature and pressure are controlled, such that dispersion and extraction of the vehicle occur substantially simultaneously by the action of the supercritical fluid. Chemicals described as being useful as supercritical fluids include carbon dioxide, nitrous oxide, sulphur hexafluoride, xenon, ethylene, chlorotrifluoromethane, ethane, and trifluoromethane.

Examples of known supercritical methods of making nanoparticles include International Patent Application No. WO 97/144407 to Pace et al., published on Apr. 24, 1997, which refers to particles of water insoluble biologically active compounds with an average size of 100 nm to 300 nm prepared by dissolving the compound in a solution and then spraying the solution into compressed gas, liquid, or supercritical fluid in the presence of appropriate surface stabilizers.

Similarly, U.S. Pat. No. 6,406,718 to Cooper et al. describes a method for forming a particulate fluticasone propionate product comprising the co-introduction of a supercritical fluid and a vehicle containing at least fluticasone propionate in solution or suspension into a particle formation vessel, the temperature and pressure in which are controlled, such that dispersion and extraction of the vehicle occur substantially simultaneously by the action of the supercritical fluid. Chemicals described as being useful as supercritical fluids include carbon dioxide, nitrous oxide, sulphur hexafluoride, xenon, ethylene, chlorotrifluoromethane, ethane, and trifluoromethane. The supercritical fluid may optionally contain one or more modifiers, such as methanol, ethanol, ethyl acetate, acetone, acetonitrile or any mixture thereof. A supercritical fluid modifier (or co-solvent) is a chemical which, when added to a supercritical fluid, changes the intrinsic properties of the supercritical fluid in or around the critical point. According to Cooper et al., the fluticasone propionate particles produced using supercritical fluids have a particle size range of 1 to 10 microns, preferably 1 to 5 microns.

7. Nano-Electrospray Techniques Used to Obtain Cinacalcet Nanoparticulate Compositions In electrospray ionization a liquid is pushed through a very small charged, usually metal, capillary. This liquid contains the desired substance, e.g., cinacalcet, dissolved in a large amount of solvent, which is usually much more volatile than the analyte. Volatile acids, bases or buffers are often added to this solution as well. The analyte exists as an ion in solution either in a protonated form or as an anion. As like charges repel, the liquid pushes itself out of the capillary and forms a mist or an aerosol of small droplets about 10 μm across. This jet of aerosol droplets is at least partially produced by a process involving the formation of a Taylor cone and a jet from the tip of this cone. A neutral carrier gas, such as nitrogen gas, is sometimes used to help nebulize the liquid and to help evaporate the neutral solvent in the small droplets. As the small droplets evaporate, suspended in the air, the charged analyte molecules are forced closer together. The drops become unstable as the similarly charged molecules come closer together and the droplets once again break up. This is referred to as Coulombic fission because it is the repulsive Coulombic forces between charged analyte molecules that drive it. This process repeats itself until the analyte is free of solvent and is a lone ion.

In nanotechnology the electrospray method may be employed to deposit single particles on surfaces, e.g., cinacalcet particles. This is accomplished by spraying colloids and ensuring that on average there is not more than one particle per droplet. Consequent drying of the surrounding solvent results in an aerosol stream of single cinacalcet particles. Here the ionizing property of the process is not crucial for the application but may be put to use in electrostatic precipitation of the particles.

D. Methods of Using the Nanoparticulate Cinacalcet Compositions of the Invention The invention also provides a method of treating a mammal in need comprising administering a stable nanoparticulate cinacalcet composition comprising: (a) particles of cinacalcet or a salt thereof having an effective average particle size of less than about 2000 nm; and (b) at least one surface stabilizer. The cinacalcet compositions of the invention may be useful in modulating parathyroid hormone secretion and serum ionized calcium levels for the purposes of treating hyperthyroidism, hypercalcemia, hyperparathyroidism, parathyroid carcinoma, or a combination thereof.

The invention provides a method of increasing bioavailability (e.g., increasing the plasma levels) of cinacalcet in a subject. Such a method comprises administering to a subject, via any pharmaceutically acceptable means, an effective amount of a composition comprising nanoparticulate cinacalcet. A preferred administration method is oral administration.

In one embodiment of the invention, the nanoparticulate cinacalcet, in accordance with standard pharmacokinetic practice, is expected to exhibit a bioavailability that is about 500% greater, about 450% greater, about 400% greater, about 350% greater, about 300% greater, about 250% greater, about 200% greater, about 150% greater, about 100% greater, about 95% greater, about 90% greater, about 85% greater, about 80% greater, about 75% greater, about 70% greater, about 65% greater, about 60% greater, about 55% greater, about 50% greater, about 45% greater, about 40% greater, about 35% greater, about 30% greater, about 20% greater, or about 10% greater than a non-nanoparticulate cinacalcet dosage form.

In another embodiment of the invention, the compositions when tested in fasting subjects in accordance with standard pharmacokinetic practice, are proposed to produces a maximum blood plasma concentration profile in less than about 6 hours, less than about 5.5 hours, less than about 5 hours, less than about 4.5 hours, less than about 4 hours, less than about 3.5 hours, less than about 3 hours, less than about 2.5 hours, less than about 2 hours, less than about 1.5 hours, less than about 1 hour, less than about 45 minutes, or less than about 30 minutes after the initial dose of the composition.

The compositions of the invention may be useful in the treatment of hyperparathyroidism, especially secondary hyperparathyroidism.

The compositions of the invention comprising nanoparticulate cinacalcet can be administered to a subject via any pharmaceutically acceptable means including, but not limited to, orally, rectally, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. In some embodiments, oral administration is preferred. As used herein, the term "subject" is used to mean an animal, preferably a mammal, including a human or non-human. The terms patient and subject may be used interchangeably.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The compositions may also comprise adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include, but are not limited to, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alginates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the drug, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

"Therapeutically effective amount" as used herein with respect to, for example a cinacalcet dosage shall mean that dosage that provides the specific pharmacological response for which cinacalcet administered in a significant number of subjects in need of such treatment. It is emphasized that "therapeutically effective amount," administered to a particular subject in a particular instance will not always be effective in treating the diseases described herein, even though such dosage is deemed a "therapeutically effective amount" by those skilled in the art. It is to be further understood that cinacalcet dosages are, in particular instances, measured as oral dosages, or with reference to drug levels as measured in blood.

One of ordinary skill will appreciate that effective amounts of cinacalcet can be determined empirically and can be employed in pure form or, where such forms exist, in pharmaceutically acceptable salt, ester, or prodrug form. Actual dosage levels of cinacalcet in the nanoparticulate compositions of the invention may be varied to obtain an amount of a cinacalcet that is effective to obtain a desired therapeutic response for a particular composition and method of administration. The selected dosage level therefore depends upon the desired therapeutic effect, the route of administration, the potency of cinacalcet, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

EXAMPLES

The following examples are provided to illustrate the present invention. It should be understood, however, that the invention is not to be limited to the specific conditions or details described in these examples. Throughout the specification, any and all references to a publicly available document, including a U.S. patent, are specifically incorporated by reference.

Examples 1-19

Preparation of Nanoparticulate Cinacalcet

The purpose of Examples 1-19 was to determine formulations and grinding conditions that would yield stable, nanoparticulate cinacalcet HCl. Different cinacalcet HCl formulations were processed under varied milling conditions. All milling was performed on a NanoMill®-01 media mill using a smooth or pegged agitator (from Elan Drug Delivery, Inc, King of Prussia, Philadelphia (U.S. Pat. No. 6,431,478)). Unless otherwise stated the chamber volume was 10 mL. In all cases, the chamber was loaded to 89% working volume* with "PolyMill® 500," 500 micron polymeric attrition media (Dow Chemical). The remaining working volume of the chamber was filled with the mixture to be milled (the "slurry"). (*The mill working volume is the milling chamber's available volume with the agitator in place.) Unless otherwise noted, the slurry density calculated on an assumed drug substance true density of 1.3 g/cm$^3$. Excipient true densities were obtained from the *Handbook of Pharmaceutical Excipients* (reference details above). The resulting nanoparticulate cinacalcet HCl dispersion (NCD) was examined first by microscopy performed with Lecia DM5000B and Lecia CTR 5000 light source (Laboratory Instruments & Supplies (I) Ltd. Ashbourne, County Meath, Republic of Ireland). Particle size analysis was carried out using a Horiba LA-910, (from Particular sciences, Hatton, Derbyshire, England).

Example 1

A formulation of cinacalcet HCl, 5.00% (w/w) (based on 100% active strength (drug purity) corresponding to 4.58% (w/w) free base), 2% (w/w) hydroxypropyl cellulose (HPC-SL), and deionised water to 100% (w/w), was milled for 60 minutes at 3000 rpm in a 10 mL chamber using a smooth agitator. The slurry density for 5% w/w slurry was calculated to 1.01 g/ml.

Microscopy observations showed discrete cinacalcet HCl nanoparticles which exhibited Brownian motion. No signs of flocculation were observed throughout the sample. Some partially milled cinacalcet HCl particles were observed but in very small numbers. No orientated growth was observed.

The nanoparticulate dispersion of cinacalcet HCl was then combined with various biorelevant media to determine the likely dissolution profile of the composition in vivo. After mixing the nanoparticulate dispersion of cinacalcet HCl with 0.1M NaCl and imaging, discrete cinacalcet HCl nanoparticles were observed which exhibited Brownian motion. For reasons discussed above, the observation of Brownian motion under the microscope was taken to be indicative of the presence of small discrete particles, the particle size of which could then be confirmed by particle size analysis. Some small degree of localized flocculation was observed but in very small amounts from microscopy assessment. After mixing the nanoparticulate dispersion of cinacalcet HCl with 0.01N HCl, discrete nanoparticles were observed which exhibited Brownian motion. No flocculation was observed from microscopy assessment.

This example demonstrates the successful preparation of a nanoparticulate cinacalcet HCl composition.

Example 2

A formulation of cinacalcet HCl 5.00% (w/w) (based on 100% active strength (drug purity) corresponding to 4.58% (w/w) free base), 1.25% (w/w) Plasdone S-630 (a random copolymer of vinyl acetate and vinyl pyrrolidone), 0.05% (w/w) docusate sodium (DOSS), and deionised water to 100% (w/w) was milled for 60 min at 3000 rpm in a 10 mL chamber using a smooth agitator.

Under microscopy, the sample appeared well dispersed with cinacalcet HCl nanoparticles clearly visible which exhibited Brownian motion. There was no evidence of flocculation. Some rod shaped particles were spread throughout the sample. This would suggest that this particular formulation (i.e., combination of drug and surface stabilizers at the particular concentrations used) could potentially be susceptible to crystal growth. The sample assayed at 4.31% w/w.

The following size distribution was observed in cinacalcet HCl saturated solution. A unimodal distribution was displayed in both samples (with or without sonication). No evidence of flocculation was present.

TABLE 5

| Sonication | Mean/nm | D50/nm | D90/nm | D95/nm | Mode/nm | Median/nm |
|---|---|---|---|---|---|---|
| N | 406 | 374 | 571 | 678 | 365 | 374 |
| Y | 432 | 402 | 610 | 724 | 412 | 402 |

This example demonstrates the successful preparation of a nanoparticulate cinacalcet HCl composition.

Example 3

A formulation of cinacalcet HCl 5.00% (w/w) (based on 100% active strength (drug purity) corresponding to 4.58% (w/w) free base), 2% (w/w) Pharmacoat 603 (hydroxypropylmethylcellulose (HPMC)), and deionised water to 100% (w/w) was milled for 60 min at 3000 rpm in a 10 mL chamber using a smooth agitator. Under microscopy, discrete cinacalcet HCl nanoparticles were observed with evidence of Brownian motion present in the sample. There were some rod like crystals visible which could indicate the presence of crystal growth.

A bi-modal distribution was displayed in the pre-sonicated sample which changed to unimodal after sonication. Thus, there appeared to be some flocculation present in the sample. The following size distribution was recorded in cinacalcet HCl saturated solution.

TABLE 6

| Mean/nm | D50/nm | D90/nm | D95/nm | Mode/nm | Median/nm | Sonication |
|---|---|---|---|---|---|---|
| 1079 | 383 | 698 | 1422 | 365 | 383 | N |
| 440 | 406 | 641 | 763 | 413 | 406 | Y |

This example demonstrates the successful preparation of a nanoparticulate cinacalcet HCl composition.

Example 4

A formulation of cinacalcet HCl 5.00% (w/w) (based on 100% active strength (drug purity) corresponding to 4.58% (w/w) free base), 1.0% (w/w) Lutrol F127 (Poloxamer 407), 1.0% (w/w) Tween 80 (polysorbate 80), and deionised water to 100% (w/w), was milled for 60 min at 3000 rpm.

Under microscopy, a large number of rod like crystals were spread throughout the sample. These crystals appeared to be agglomerated to form larger crystals. This would indicate that the formulation is very susceptible to crystal growth. There was no evidence of Brownian motion. The following size distribution was observed in cinacalcet HCl saturated solution.

TABLE 7

| Mean/nm | D50/nm | D90/nm | D95/nm | Mode/nm | Median/nm | Sonication |
|---|---|---|---|---|---|---|
| 1413 | 537 | 4140 | 6390 | 471 | 537 | N |
| 2470 | 753 | 7289 | 10644 | 482 | 753 | Y |

While having a $D_{50}$ of less than 2000 nm this nanoparticulate cinacalcet HCl composition, with the particular combination of drug and surface stabilizers at the particular concentrations used, showed unfavorable agglomeration and/or crystal growth characteristics that would have to be addressed for the further development of this formulation to be progressed.

Example 5

A formulation of cinacalcet HCl 5.00% (w/w) (based on 100% active strength (drug purity) corresponding to 4.58% (w/w) free base), 1.5% (w/w) Pluronic F108, and deionised water to 100% (w/w/) was initially milled for 60 min and then subjected to a further 30 min (i.e. 90 min in total) at 3000 rpm (smooth agitator).

Under microscopy, a large number of rod shaped crystals were present throughout the slide. No evidence of cinacalcet HCl nanoparticles or Brownian motion was noted. The rod like crystals would suggest that the formulation is very susceptible to crystal growth. The following size distribution was observed in cinacalcet HCl saturated solution for samples removed from the mill at the 60 and 90 min time points.

TABLE 8

| Mean/nm | D50/nm | D90/nm | D95/nm | Mode/nm | Median/nm | 60 seconds sonication | Milling time |
|---|---|---|---|---|---|---|---|
| 1044 | 538 | 2433 | 3858 | 471 | 538 | N | 60 |
| 959 | 607 | 2034 | 2926 | 480 | 607 | Y | 60 |
| 1211 | 453 | 3660 | 6198 | 416 | 453 | N | 90 |
| 1669 | 526 | 5347 | 8178 | 471 | 526 | Y | 90 |

Again, while having a $D_{50}$ of less than 2000 nm this nanoparticulate cinacalcet HCl composition, with the particular combination of drug and surface stabilizers at the particular concentrations used, showed unfavorable agglomeration and/or crystal growth characteristics that would have to be addressed for the further development of this formation to be progressed.

Example 6

A formulation of cinacalcet HCl 5.00% (w/w) (based on 100% active strength (drug purity) corresponding to 4.58% (w/w) free base), 2% (w/w) HPC-SL, and 93.04% (w/w) deionised water was milled for 60 min at 3000 rpm (smooth agitator).

Under microscopy, the sample appeared to be well dispersed with discrete cinacalcet HCl nanoparticles which exhibited Brownian motion. There were no signs of crystal growth or flocculation.

Stability of the milled nanoparticulate cinacalcet HCl composition was tested by measuring the cinacalcet HCl particle size over time. The samples were stored at 5° C. for 0, 6 and 13 days and the following size distribution was observed in cinacalcet HCl saturated solution.

TABLE 9

| Mean/nm | D50/nm | D90/nm | D95/nm | Mode/nm | Median/nm | 60 seconds sonication | Storage time |
|---|---|---|---|---|---|---|---|
| 306 | 297 | 415 | 455 | 312 | 297 | N | 0 |
| 308 | 299 | 418 | 458 | 313 | 299 | Y | 0 |
| 324 | 315 | 440 | 490 | 317 | 315 | N | 6 |
| 327 | 318 | 442 | 492 | 318 | 318 | Y | 6 |
| 332 | 321 | 456 | 505 | 319 | 321 | N | 13 |
| 345 | 332 | 477 | 531 | 321 | 332 | Y | 13 |

In the composition assayed immediately after milling a good unimodal distribution was displayed in both pre- and post-sonication analysis. After 6 days storage, a unimodal distribution was observed with no signs of flocculation pre or post sonication.

This example demonstrates the successful preparation of a nanoparticulate cinacalcet HCl composition.

Example 7

A formulation of cinacalcet HCl 5.00% (w/w) (based on 100% active strength (drug purity) corresponding to 4.58% (w/w) free base), 2% (w/w) Plasdone S-630, and 93.04% (w/w) deionised water was milled for 60 min at 3000 rpm (smooth agitator). Under microscopy, the sample appeared well dispersed with some rod shaped crystals visible. No signs of flocculation or crystal growth was observed and Brownian motion was clearly visible. There were signs of some unmilled cinacalcet HCl present.

The samples were stored at 5° C. for 0 and 7 days and the following size distribution was observed in cinacalcet HCl saturated solution.

TABLE 10

| Mean/nm | D50/nm | D90/nm | D95/nm | Mode/nm | Median/nm | 60 seconds sonic'n | Storage time |
|---|---|---|---|---|---|---|---|
| 374 | 344 | 536 | 639 | 322 | 344 | N | 0 |
| 394 | 356 | 571 | 703 | 360 | 356 | Y | 0 |
| 427 | 364 | 625 | 873 | 361 | 364 | N | 7 |
| 477 | 387 | 737 | 1126 | 365 | 387 | Y | 7 |

In the composition assayed at T0, the particle size analysis showed a unimodal distribution in both pre- and post-sonication with a presonication $D_{Mean}$ of 0.374 µm. After 7 days storage, a unimodal distribution was observed with no signs of flocculation.

This example demonstrates the successful preparation of a nanoparticulate cinacalcet HCl composition.

Example 8

A formulation of cinacalcet HCl 5.00% (w/w) (based on 100% active strength (drug purity) corresponding to 4.58% (w/w) free base), 2% (w/w) Plasdone K29/32 (polyvinylpyrrolidone), and 93.04% (w/w) deionised water was milled for 60 min at 3000 rpm (smooth agitator).

Under microscopy, the sample seemed to be well dispersed with cinacalcet HCl nanoparticles which exhibited Brownian motion. Some partially milled material was also observed, and rod shaped crystals were also observed throughout the sample which could be representative of crystal growth.

The samples were stored at 5° C. for 0, 6 and 15 days and the cinacalcet HCl particle size distribution presented below was observed in cinacalcet HCl saturated solution.

TABLE 11

| Mean/nm | D50/nm | D90/nm | D95/nm | Mode/nm | Median/nm | 60 seconds sonication | Storage time |
|---|---|---|---|---|---|---|---|
| 441 | 390 | 652 | 847 | 367 | 390 | N | 0 |
| 472 | 409 | 715 | 959 | 412 | 409 | Y | 0 |
| 378 | 353 | 539 | 630 | 360 | 353 | N | 6 |
| 396 | 370 | 566 | 660 | 364 | 370 | Y | 6 |
| 539 | 432 | 922 | 1301 | 414 | 432 | N | 15 |
| 645 | 496 | 1211 | 1579 | 421 | 496 | Y | 15 |

All particle sizes were determined to be well below the 2000 nm level. Furthermore, the observed changes in particle size over time are small indicative of the successful preparation of a stable nanoparticulate cinacalcet HCl composition.

Example 9

A formulation of cinacalcet HCl 4.96% (w/w) (corresponding to 4.54% (w/w) free base), 2% (w/w) Plasdone C-30, and 93.04% (w/w) deionised water was milled for 60 min at 3000 rpm in a 10 mL chamber using a pegged agitator.

Under the Lecia microscope, cinacalcet HCl nanoparticles were observed which exhibited Brownian motion. Some flocculation was apparent across the aliquot of neat nanoparticulate cinacalcet HCl dispersion analysed by microscopy and rod like crystals were also observed. This could be an indication of crystal growth. The following size distribution was observed in cinacalcet HCl saturated solution.

TABLE 12

| Mean/nm | D50/nm | D90/nm | D95/nm | Mode/nm | Median/nm | 60 seconds sonication |
|---|---|---|---|---|---|---|
| 772 | 362 | 620 | 1209 | 361 | 362 | N |
| 413 | 384 | 582 | 694 | 367 | 384 | Y |

This example demonstrates the successful preparation of another nanoparticulate cinacalcet HCl composition.

Example 10

A formulation of cinacalcet HCl (4.96% (w/w)), HPC-SL (2.00% (w/w)), docusate sodium (0.02% (w/w)), and deionised water (to 100% (w/w)), was milled for 60 min at 3000 rpm (smooth agitator).

Under the microscope, cinacalcet HCl nanoparticles were observed which exhibited Brownian motion. There were some small rod-like crystals visible along with some unmilled cinacalcet HCl. The following size distribution was observed in cinacalcet HCl saturated solution, after storage at 5° C.

TABLE 13

| Mean/nm | D50/nm | D90/nm | D95/nm | Mode/nm | Median/nm | 60 seconds sonication | Storage (day) |
|---|---|---|---|---|---|---|---|
| 330 | 320 | 446 | 497 | 319 | 320 | N | 0 |
| 335 | 326 | 454 | 501 | 321 | 326 | Y | 0 |
| 399 | 379 | 560 | 639 | 367 | 379 | N | 7 |
| 406 | 377 | 575 | 679 | 366 | 377 | N (Repeat) | 7 |
| 442 | 410 | 631 | 749 | 414 | 410 | Y | 7 |

This composition demonstrated good particle size and stability characteristics and represents the successful preparation of a further nanoparticulate cinacalcet HCl composition.

Example 11

A formulation of cinacalcet HCl (4.96% (w/w)), Plasdone K17 (polyvinylpyrrolidone (PVP)) (1.25% (w/w)), docusate sodium (DOSS) (0.05% (w/w)) and deionised water to 100% (w/w) was milled for 60 min at 3000 rpm (smooth agitator).

Under microscopy, cinacalcet HCl nanoparticles were observed which exhibited Brownian motion. Severe flocculation was observed across the aliquot of nanoparticulate cinacalcet HCl dispersion being analysed under the microscope and partially-unmilled cinacalcet HCl was also present. The following size distribution was observed in cinacalcet HCl saturated solution

TABLE 14

| Mean/nm | D50/nm | D90/nm | D95/nm | Mode/nm | Median/nm | 60 seconds sonication |
|---|---|---|---|---|---|---|
| 442 | 348 | 700 | 1117 | 320 | 348 | N |
| 377 | 357 | 531 | 609 | 362 | 357 | Y |

A unimodal distribution is seen both pre and post. The reduction in particle size following sonication is attributed to the breakdown of weakly flocculated aggregates (the flocculation observed using microscopy) upon agitation (sonication) of the sample.

This example demonstrates the successful preparation of a further nanoparticulate cinacalcet HCl composition.

Example 12

A formulation of cinacalcet HCl (4.96% (w/w)), Lutrot F68 (poloxamer 188) (1.25% (w/w)), deoxycholic acid sodium salt (0.05% (w/w)), and deionised water to 100% (w/w) was milled for 60 min at 3000 rpm (smooth agitator).

Under microscopy the sample appeared well dispersed with cinacalcet HCl nanoparticles which exhibited Brownian motion. There were no signs of crystal growth or flocculation.

TABLE 15

| Mean/nm | D50/nm | D90/nm | D95/nm | Mode/nm | Median/nm | 60 seconds sonication |
|---|---|---|---|---|---|---|
| 437 | 405 | 640 | 755 | 413 | 405 | N |
| 472 | 437 | 692 | 821 | 419 | 437 | Y |

This composition demonstrates good particle size characteristics, well below the 2000 nm level, and again demonstrates the successful preparation of a nanoparticulate cinacalcet HCl composition.

Example 13

This experiment examined the stability over time of a single formulation stored under different conditions. Cinacalcet HCl (5.00% (w/w)) and HPC-SL (2% (w/w)) in deionised water (to 100% (w/w)) was milled for 60 min at 2400 rpm (pegged agitator).

Table 16 shows observations of the sample for each time point (T in days) and storage condition (temperature in ° C. and relative humidity "RH"), the observations of the particles under microscopy, the pH and % w/w of cinacalcet in the sample. ("T0" represents the day on which the dispersion was prepared and "Tx" is x days after T0; "NP" means test not performed, or parameter not measured.)

Table 17 shows the analysis of the cinacalcet HCl particle size and distribution for various stability time points and conditions. Column 1 shows time point and storage conditions using the same numbering system as that described for Table 16. (The medium in which particle size analysis was carried out was a saturated solution of cinacalcet hydrochloride.)

TABLE 16

| Stability time point (days) and storage | Microscopy Observation | pH | Assay (% w/w) |
|---|---|---|---|
| T0 5° C. 25° C./60% RH 40° C./75% RH | Cinacalcet HCl nanoparticles were observed which exhibited Brownian motion. Some small rod shaped crystals. | NP | T 1 Timepoint 5° C. sample –4.95% w/w 25° C./60% RH sample –4.98% w/w 40° C./75% RH sample –4.97% w/w |
| T3 5° C. | — | NP | NP |
| T3 25° C./60% RH | — | NP | NP |
| T3 40° C./75% RH | — | NP | NP |
| T9 (5° C.) | — | NP | NP |
| T11 (5° C.) | Cinacalcet HCl nanoparticles were observed which exhibited Brownian motion. Small rod shaped crystals visible. | 4.94 | T 8 Timepoint 5° C. sample –4.96% w/w |
| T11 25° C./60% RH | Cinacalcet HCl nanoparticles were observed which exhibited Brownian motion. Small rod shaped crystals visible. | 4.99 | T 8 Timepoint 25° C./60% RH sample –5.06% w/w |
| T11 40° C./75% RH | Cinacalcet HCl nanoparticles were observed which exhibited Brownian motion. More rod shaped crystals visible at 40° C. than at 25° C. and 5° C.. | 5 | T 8 Timepoint 40° C./75% RH sample –5.01% w/w |

TABLE 16-continued

| Stability time point (days) and storage | Microscopy Observation | pH | Assay (% w/w) |
|---|---|---|---|
| T16 (5° C.) | Cinacalcet HCl nanoparticles were observed which exhibited Brownian motion. Some small rod shaped crystals observed. No flocculation was seen through the sample. | NP | T 15 Timepoint 5° C. sample −4.95% w/w |
| T16 25° C./ 60% RH | Cinacalcet HCl nanoparticles were observed which exhibited Brownian motion. Rod shaped crystals observed-these were slightly larger and more numerous than seen in the 5° C. sample.. No flocculation present at this time point. | NP | T 15 Timepoint 25° C./60 %RH sample −4.98% w/w |
| T16 (40° C./ 75% RH) | Cinacalcet HCl nanoparticles were observed which exhibited Brownian motion. Rod shaped crystals observed-slightly larger and more numerous than seen in the 5° C. & 25° C. sample. No flocculation was seen through the sample. | NP | T 15 Timepoint 40° C./75% RH sample −4.97% w/w |
| T25 (5° C.) | Cinacalcet HCl nanoparticles were observed which exhibited Brownian motion some rod shaped crystals were present more than at (T16) no signs of flocculation were present through this sample | NP | T 23 Timepoint 5° C. sample −4.93% w/w |
| T25 (25° C./ 60% RH) | Cinacalcet HCl nanoparticles were observed which exhibited Brownian motion. Larger and more rod shaped crystals were observed than in the previous microscopy (at T16). No flocculation was seen at this point across the sample. | NP | T 23 Timepoint 25° C./60% RH sample −4.96% w/w |
| T25 (40° C./ 75% RH) | Cinacalcet HCl nanoparticles were observed which exhibited Brownian motion. More rod shaped crystals appeared to have formed- larger in size than the previous microscopy sample shows (at T16). A slight small patch interpreted as flocculation was also observed | NP | T 23 Timepoint 40° C./75% RH sample −4.93% w/w |
| T29 (5° C.) | Cinacalcet HCl nanoparticles were observed that exhibited Brownian motion. Rod shaped crystals were present across the sample however not in great amounts. No flocculation was present. | NP | T 31 Timepoint 5° C. sample −5.03% w/w |
| T29 (25° C./60% RH) | Cinacalcet HCl nanoparticles were observed that exhibited Brownian motion .Rod shaped crystals were present across the sample- longer and more numerous than in the 5° C. sample. No flocculation. | NP | T 31 Timepoint 25° C./60% RH sample −5.04% w/w |
| T29 (40° C./75% RH) | Cinacalcet HCl nanoparticles were observed which exhibited Brownian motion. Rod shaped crystals were seen across the sample- larger and more numerous than in the 5° C. and the 25° C. samples. No flocculation | NP | T 31 Timepoint 40° C./75% RH sample −4.99% w/w |
| T30 (5° C.) | — | 4.77 | NP |
| T30 (25° C./ 60% RH) | — | 5.3 | NP |
| T30 (40° C./ 75% RH) | — | 4.82 | NP |
| T38 (5° C.) | Microscopy was performed by placing 5 μl of the nanoparticulate dispersion of cinacalcet HCl onto a glass slide and imaging directly. Although very concentrated, the nanoparticulate dispersion of cinacalcet HCl appeared to be composed of discrete cinacalcet HCl nanoparticles which exhibited Brownian motion. No flocculation was observed upon assessment of the nanoparticulate dispersion of cinacalcet HCl. | NP | NP |
| | Microscopy was performed by mixing 5 μls of the nanoparticulate dispersion of cinacalcet HCl into 5 μls of 0.1M NaCl solution. Post mixing imaging showed the nanoparticulate dispersion of cinacalcet HCl to be well dispersed with no signs of flocculation. Larger rod like crystals were observed which are characteristic of crystal growth. The nanoparticulate dispersion of cinacalcet HCl overall appeared well dispersed with discrete cinacalcet HCl nanoparticles exhibiting Brownian motion. | NP | NP |
| | Microscopy was performed by mixing 5 μls of the nanoparticulate dispersion of cinacalcet HCl into 5 μls of 0.01 Normal solution. Post mixing imaging showed the nanoparticulate dispersion of cinacalcet HCl to be composed of | NP | NP |

TABLE 16-continued

| Stability time point (days) and storage | Microscopy Observation | pH | Assay (% w/w) |
|---|---|---|---|
| | discrete nanoparticles which exhibited Brownian motion. Larger crystals were observed which indicated are crystal growth. Flocculation was not apparent from a thorough assessment of the dispersion via microscopy. | | |
| T38 (25° C./60% RH) | — | NP | NP |
| T38 (40° C./75% RH) | — | NP | NP |

TABLE 17

| Stability time point (days) and storage | PS Medium | Mean/ nm | D50 | D90 | D95 | Mode | Med. | sonic | Particle size Observation |
|---|---|---|---|---|---|---|---|---|---|
| T0 5° C. 25° C./60% RH 40° C./75% RH | Sat. Soln | 380 395 | 361 377 | 533 552 | 606 625 | 363 367 | 361 377 | N Y | A unimodal distribution is seen both pre and post sonication with a D50 of 361 nm pre and a D50 377 nm post sonication |
| T3 5° C. | Sat. Soln | 433 559 | 404 500 | 617 844 | 731 1042 | 412 477 | 404 500 | N Y | A unimodal distribution observed with no flocculation pre and post sonication. |
| T3 25° C./60% RH | Sat. Soln | 426 456 614 | 396 415 532 | 609 661 989 | 725 824 1224 | 411 414 481 | 396 415 532 | N (Rept) N Y | A unimodal distribution was observed with no signs of flocculation for both pre and post sonication. The dispersion cinacalcet HCl particle size was observed to increase post sonication suggesting a weakly absorbed stabiliser to the nanoparticle cinacalcet HCl surface. The D mean partial increased from 380 nm (at T0)to 456 nm at T 3 at 25° c./60% RH |
| T3 40° C./75% RH | Sat. Soln | 466 574 | 419 490 | 679 946 | 858 1199 | 415 473 | 419 490 | N Y | Unimodal distribution was observed with no apparent sign of flocculation both pre and post sonication. The dispersion cinacalcet HCl particle size was observed to increase post sonication suggesting weakly absorbed stabilization of the homopolymer employed. The D mean particle size appears to have increased from 380 nm (at T0) to 466 nm at day 3 at 40° c./75% RH. |
| T9 (5° C.) | Sat. Soln | 380 389 | 351 358 | 545 559 | 645 664 | 359 361 | 351 358 | N Y | A unimodal distribution was seen both pre and post sonication with a mean value pre sonication of 380 nm on T 9 stored at 5° c. (T0) was also 380 nm for the mean value pre sonication. |
| | Sat. Soln | 381 387 | 355 360 | 546 557 | 639 653 | 360 362 | 355 360 | N Y | A unimodal distribution was observed for both pre and post sonication with a mean value of 381 nm pre sonication and 387 post sonication on T 9 of manufacture and stored at 5° c. A reduction of 52 nm. |
| T11 (5° C.) | Sat. Soln | 412 429 | 380 396 | 592 624 | 714 747 | 366 411 | 380 396 | N Y | A unimodal distribution was seen for both pre and post sonication with a mean value increase of 32 nm from (T0) to (T11) |
| T11 25° C./60% RH | Sat. Soln | 422 454 | 383 404 | 615 676 | 755 868 | 366 411 | 383 404 | N Y | A unimodal distribution was seen for both pre and post sonication with a mean value increase of 42 nm from (T0) to (T11) |
| T11 40° C./75% RH | Sat. Soln | 441 471 | 385 406 | 665 732 | 881 980 | 365 411 | 385 406 | N Y | A unimodal distribution was seen for both pre and post sonication with a mean value increase of 61 nm from (T0) to (T11) |
| T16 (5° C.) | Sat. Soln | 407 424 | 370 382 | 587 623 | 722 767 | 363 365 | 370 382 | N Y | A unimodal distribution was seen for both pre and post sonication with a mean value increase from 380 nm(T0) to 407 nm (T16) an increase of 27 nm. |
| T16 25° C./60% RH | Sat. Soln | 447 513 | 395 450 | 666 803 | 869 1025 | 367 419 | 395 450 | N Y | A unimodal distribution was seen for both pre and post sonication with a mean value increase of 67 nm from (T0) to (T16) |
| T16 (40° C./75% RH) | Sat. Soln | 489 593 | 408 485 | 787 1023 | 1097 1334 | 368 471 | 408 485 | N Y | A unimodal distribution was seen for both pre and post sonication with a mean value shows an increase of 109 nm from(T0) |
| T25 (5° C.) | Sat. Soln | 445 506 | 395 430 | 662 817 | 854 1089 | 367 415 | 395 430 | N Y | A unimodal distribution was seen for both pre and post sonication; a tail has formed which is on the higher side of the distribution range this would normally be a sign of crystal growth. The (T0)was 380 nm and the (T25) shows a pre sonication mean value 0f 445 nm an increase of 65 nm. |
| T25 (25° C./60% RH) | Sat. Soln | 450 497 | 392 417 | 674 799 | 899 1101 | 366 412 | 392 417 | N Y | A unimodal distribution was seen both pre and post sonication with a tail forming to the higher side of the distribution range this would suggest signs of crystal growth. The mean value pre sonication at (T0) was 380 nm and at (T25) 450 nm an increase of 70 nm. |

TABLE 17-continued

| Stability time point (days) and storage | PS Medium | Mean/ nm | D50 | D90 | D95 | Mode | Med. | sonic | Particle size Observation |
|---|---|---|---|---|---|---|---|---|---|
| T25 (40° C./75% RH) | Sat. Soln | 568 618 | 445 470 | 1011 1142 | 1389 1538 | 415 417 | 445 470 | N Y | A unimodal distribution was seen both pre and post sonication. With this sample a tail has formed to the higher side of the distribution range which could suggest crystal growth. The (T0) mean value pre sonication was 380 nm and at (T25) 568 nm an increase of 188 nm. |
| T29 (5° C.) | Sat. Soln | 406 425 | 365 378 | 590 628 | 738 795 | 362 364 | 365 378 | N Y | A unimodal distribution was seen both pre and post sonication. The mean value pre sonication for (T29) was 406 nm and at (T0) was 380 nm which shows an increase of 26 nm this together with a small tail forming to the higher side of the distribution range could suggest crystal growth. The (T25) time point shows a larger increase of 65 nm as oppose to the (T29) at 26 nm |
| T29 (25° C./60% RH) | Sat. Soln | 410 427 | 363 377 | 599 635 | 763 824 | 361 364 | 363 377 | N Y | A unimodal distribution was seen both pre and post sonication with the (T29) pre sonication mean value at 410 nm and the (T0) 380 nm shows an increase of 30 nm this however is less than the (T25) which has 70 nm from (T0). A slight tail is still present on the higher side of the distribution range which could suggest some crystal growth. |
| T29 (40° C./75% RH) | Sat. Soln | 513 512 | 400 404 | 896 891 | 1281 1263 | 365 365 | 400 404 | N Y | A unimodal distribution was seen both pre and post sonication with the (T29) pre sonication mean value at 513 nm and the(T0) 380 nm this shows an increase of 133 nm this is lower than the(T25) which increased from (T0) by 188 nm. A tail has formed on the higher side of the distribution range this would suggest crystal growth. |
| T38 (5° C.) | Sat. Soln | 431 470 616 | 386 413 486 | 634 708 1125 | 797 929 1464 | 366 413 420 | 386 413 486 | N Y Y | A unimodal distribution was seen both pre and post sonication flocculation was not observed. After 38 days at 5° c. the formulation D Mean particle size increased from 380 nm to 431 nm |
| T38 (25° C./60% RH) | Sat. Soln | 435 499 | 384 423 | 644 781 | 835 1076 | 365 414 | 384 423 | N Y | A unimodal particle size distribution was observed both pre and post sonication. No flocculation was evident from assessment of the particle size |
| T38 (40° C./75% RH) | Sat. Soln | 514 524 543 | 407 417 428 | 890 907 951 | 1262 1272 1321 | 366 411 413 | 407 417 428 | N N Y | A unimodal distribution was seen both pre and post sonication with no apparent signs of flocculation observed from the particle size data. (Second line of data derived from repeat analysis of a second aliquot.) |

Example 14

In this example the water dispersion medium was replaced with phosphate buffer at the same ratio. A formulation of cinacalcet HCl (5.00% (w/w) equivalent to 4.54% (w/w) free base), HPC-SL (2% (w/w)), and sodium hydroxide-potassium dibsic phosphate (pH=5) to 100% (w/w) was milled for 60 min at 3000 rpm in a 10 mL chamber using a smooth agitator.

The cinacalcet HCl size distribution presented below was observed in cinacalcet HCl saturated solution. A unimodal distribution was displayed pre- and post-sonication. There was no evidence of flocculation.

TABLE 18

| Mean/ nm | D50/ nm | D90/ nm | D95/ nm | Mode/ nm | Median/ nm | 60 seconds sonication |
|---|---|---|---|---|---|---|
| 196 | 185 | 259 | 296 | 183 | 185 | N |
| 197 | 188 | 257 | 293 | 184 | 188 | Y |

(Under microscopy the sample seemed to be severely flocculated with no signs of Brownian motion. There was however no evidence of flocculation during particle size analysis. These different observations may be down to dilution effects on the buffering environment used in the Horiba instrument during particle size analysis.

This example demonstrates the successful preparation of a nanoparticulate cinacalcet HCl composition.

Example 15

This experiment examined the effect of further additional variables on cinacalcet HCl particle size and stability, of a formulation comprising cinacalcet HCl (5.00% (w/w)), HPC-SL (2% (w/w)) in deionized water (to 100% (w/w), milled initially for 60 min and then for a further 15 min (i.e. a total milling time of 75 min), at 2400 rpm in a 50 mL chamber using a pegged agitator The following cinacalcet HCl size distribution was observed.

TABLE 19

| Milling | Mean/ nm | D50/ nm | D90/ nm | D95/ nm | Mode/ nm | Median/ nm | 60 seconds sonication |
|---|---|---|---|---|---|---|---|
| 2400 rpm/ 60 min | 356 362 | 343 349 | 494 500 | 554 560 | 359 360 | 343 349 | N Y |
| 2400 rpm/+15 min (i.e. total 75 min) | 353 367 | 343 357 | 485 500 | 537 557 | 359 363 | 343 357 | N Y |

After 60 minutes, a unimodal distribution was seen for both pre- and post-sonication. The Dmean value pre-sonication was 356 nm and post-sonication 362 nm. Further milling was then conducted. Following further milling (i.e. additional 15 min) the composition was observed to maintain a unimodal distribution, with minimal change in particle size.

Post milling the cinacalcet HCl size distribution presented below was observed. In 0.1M NaCl a unimodal distribution was seen for both pre- and post-sonication with the D mean of 337 nm. Under microscopy, cinacalcet HCl nanoparticles were observed that exhibited Brownian motion. In 0.01N HCl, a unimodal distribution was seen for both pre- and post-sonication with the Dmean value at 357 nm. Under microscopy, cinacalcet HCl nanoparticles were observed that clearly exhibited Brownian motion.

TABLE 20

| PS Medium | Mean/ nm | D50/ nm | D90/ nm | D95/ nm | Mode/ nm | Median/ nm | 60 seconds sonication |
|---|---|---|---|---|---|---|---|
| Cinacalcet HCl Saturated Solution | 337 | 329 | 453 | 498 | 322 | 329 | N |
| | 350 | 343 | 472 | 510 | 359 | 343 | Y |

In a saturated solution of cinacalcet HCl, a unimodal distribution was seen for both pre- and post-sonication. Under microscopy, cinacalcet HCl nanoparticles were observed that clearly exhibited Brownian motion. Some very small rod shaped crystals were present which could suggest crystal growth.

After storage at 5° C. for 8 days, the cinacalcet HCl particle size distribution presented below was observed. In a saturated solution of cinacalcet, a unimodal distribution was seen for both pre- and post-sonication with the mean value at 350 nm, an increase of 13 nm since T0 (337 nm).

TABLE 21

| PS Medium | Mean/ nm | D50/ nm | D90/ nm | D95/ nm | Mode/ nm | Median/ nm | 60 seconds sonication |
|---|---|---|---|---|---|---|---|
| Cinacalcet HCl Saturated Solution | 350 | 340 | 479 | 527 | 358 | 340 | N |
| | 377 | 367 | 510 | 569 | 365 | 367 | Y |

By comparison the distribution presented below was observed after 8 days storage at 25° C. and 60% relative humidity. In a saturated solution of cinacalcet, a unimodal distribution was seen for both pre- and post-sonication with the D mean value of 336 nm at T8, compared with 357 nm at T0: a very slight decrease of 1 nm.

TABLE 22

| PS Medium | Mean/ nm | D50/ nm | D90/ nm | D95/ nm | Mode/ nm | Median/ nm | 60 seconds sonication |
|---|---|---|---|---|---|---|---|
| Cinacalcet HCl Saturated Solution | 336 | 326 | 457 | 504 | 320 | 326 | N |
| | 353 | 343 | 484 | 536 | 359 | 343 | Y |

After storage at 5° C. for 14 days, the following cinacalcet HCl size distribution was observed.

TABLE 23

| PS Medium | Mean/ nm | D50/ nm | D90/ nm | D95/ nm | Mode/ nm | Median/ nm | 60 seconds sonication |
|---|---|---|---|---|---|---|---|
| Cinacalcet HCl Saturated Solution | 328 | 319 | 443 | 493 | 319 | 319 | N |
| | 328 | 320 | 442 | 491 | 319 | 320 | Y |

This example demonstrates the successful preparation of a nanoparticulate cinacalcet HCl composition.

Example 16

A formulation of cinacalcet HCl (5.00% (w/w), HPC-SL (2% (w/w)), and deionised water to 100% (w/w) was milled for 60 min at 1333 rpm in a 50 mL chamber using a smooth agitator.

Undiluted, the cinacalcet HCl nanoparticles exhibited Brownian motion, with no signs of flocculation. When diluted in saturated cinacalcet HCl solution, cinacalcet HCl nanoparticles were observed and these clearly exhibited Brownian motion. There were no signs of flocculation present across the sample. There were no signs of flocculation across the sample although some very small rod shaped crystals were observed across the slide. The particle size of cinacalcet HCl particles are set out in the following table.

TABLE 24

| PS Medium | Mean/ nm | D50/ nm | D90/ nm | D95/ nm | Median/ nm | Mode/ nm | 60 s sonic'n |
|---|---|---|---|---|---|---|---|
| Cinacalcet HCl Saturated Solution | 244 | 224 | 366 | 423 | 224 | 212 | N |
| | 289 | 279 | 395 | 439 | 279 | 278 | Y |

In cinacalcet HCl saturated solution, a unimodal distribution was seen for both pre- and post-sonication with a mean value of 244 nm.

This example demonstrates the successful preparation of a nanoparticulate cinacalcet HCl composition.

Example 17

In order to assess the in vivo performance of a nanoparticulate cinacalcet composition according to the invention a formulation of cinacalcet HCl (5.00% (w/w) (4.54% (w/w) free base)), HPC-SL (2% (w/w)), and deionised water (to 100.00% (w/w)) was prepared by milling the mixture in a 50 mL chamber to produce a cinacalcet dispersion having $D_{mean}$ of approximately 350 nm/$D_{50}$ of approximately 335 nm; particle size measured without any sonication in a saturated solution of cinacalcet HCl (in this context approximately means +/−5%). The slurry density was measured prior to milling at 1.01 g/mL at 21.2° C. Under microscopy, the dispersion was composed of discrete cinacalcet HCl nanoparticles which exhibited Brownian motion. No flocculation was observed. Separate dispersions (Treatments A and C in Example 18 below) having the abovementioned particle size characteristics were prepared in advance of the fasted and fed legs of the biostudy described in the following Example.

Example 18

Fed/Fast Pharmacokinetics of Oral Nanocrystal Dispersion and Mimpara® Tablets

The objective of this study was to determine the pharmacokinetics of cinacalcet when administered orally as cinacalcet hydrochloride (50 mg/g) (5% w/w) in a nanoparticulate dispersion and as a 30 mg cinacalcet (as hydrochloride) Mimpara® tablet to fasted and fed male beagle dogs. The amount of cinacalcet in the nanoparticulate dispersion and the Mimpara® tablets was comparable and both contained 33 mg cinacalcet hydrochloride. The label of the Mimpara® tablet (30 mg) relates to the amount of cinacalcet free base in the formulation.

Study Design

This biostudy was an open label, 4 treatments, 4 periods, un-randomized design study. Six dogs received all four treatments. There was an eleven day wash out period between Period 1 and 2 and a ten day wash out period between Period 2 and 3 and Period 3 and 4. The treatments administered in this study were as follows:

Treatment A: 0.66 grams of a cinacalcet hydrochloride (50 mg/g) (5% w/w) nanoparticulate dispersion (oral) administered fasted (prepared as per Example 17)

Treatment B: 30 mg cinacalcet (as 33 mg cinacalcet hydrochloride) Mimpara® tablet (oral) administered fasted Treatment C: 0.66 grams of a cinacalcet hydrochloride (50 mg/g) (5% w/w) nanoparticulate dispersion (oral) administered fed (prepared as per Example 17)

Treatment D: 30 mg cinacalcet (as 33 mg cinacalcet hydrochloride) Mimpara® tablet (oral) administered fed Blood samples were collected on Study Days 0, 12, 23 ad 34 at the following time points: Before dosing and at 30 minutes (±1 minute), 1 hour (±1 minute), 1.5 hours (±minute), 2 hours (±minute), 2.5 hours (±minute), 3 hours (±1 minute), 4 hours (±1 minute), 5 hours (±1 minute), 6 hours (±1 minute), 7 hours (±1 minute), 8 hours (±1 minute) and 12 hours (±1 minute) after dosing. On Study Days 1, 13, 24 and 35 blood samples were collected at 20 hours (±5 minutes), 24 hours (±5 minutes), 30 hours (±5 minutes) and 36 hours (±5 minutes) after dosing. On Study Day 2, 14, 25 and 36 blood samples were collected at 45 hrs (±5 minutes) after dosing.

Methodology

Bioanalysis Methodology

Cinacalcet was measured in dog plasma samples by a validated LC MS/MS method. The analytical method used involved the extraction of cinacalcet and its internal standard fenbendazole from plasma by solid phase extraction before injection onto the LC/MS/MS system. The standard curves for the analytical runs in the study covered the concentration range of 0.5-50 ng/ml with a limit of quantitation of 0.5 ng/ml for cinacalcet.

Pharmacokinetics Methodology

The pharmacokinetic parameters were calculated using WinNonlin™, Version 4.0.1 (Pharsight Corporation, USA). The following pharmacokinetic parameters were derived from the plasma concentrations versus time data for cinacalcet using non-compartmental methodology:

$AUC_{inf}$ ($AUC_{0-\infty}$)—Area under the curve from time of dosing extrapolated to infinity as $AUC_{0-t}+C_{last}$/lambda z, where $AUC_{0-t}$ is the area under the curve from time of dosing to the last evaluable concentration, $C_{last}$ is the last evaluable plasma concentration and lambda z is the elimination rate constant associated with the terminal portion of the curve.

$AUC_{last}$ ($AUC_{0-t}$)—Area under the curve from the time of dosing to the time of the last quantifiable concentration calculated using the linear trapezoidal rule where AUC $(t_1-t_2)=\delta t^*(c_2+c_1)/2$.

Maximum plasma concentration ($C_{max}$) and its corresponding time ($t_{max}$) were recorded from the observed plasma concentration-time profiles.

Relative bioavailability of the test treatment (Trt A) to the reference (Trt B) based on AUC (test/reference and expressed as a percentage).

Half Life ($t_{1/2}$) was calculated as ln 2/Lambda z.

Lambda z ($K_{el}$)—First order rate constant associated with the terminal (log-linear) portion of the curve estimated via linear regression of time vs. log concentration. For each regression analysis, an adjusted $r^2$ was computed as follows: Adjusted $r^2=1-((1-r^2)*(n-1))/(n-2)$, where $r^2$ is the square of the correlation coefficient and n is the number of points used in the regression. Linear regression analyses of time versus log plasma concentration was conducted using a manual iterative procedure including increasing numbers of samples from the last three quantifiable plasma concentrations up to and including $C_{max}$. The regression with the largest adjusted $r^2$ was selected to estimate lambda z as −1 times the estimated slope of the regression line.

As there were no significant deviations from the amount of cinacalcet administered in each of the administrations or the actual sampling times at which blood draws were obtained, pharmacokinetic analysis was based on nominal amounts administered and nominal sampling times. For ease of comparison, the plasma concentrations versus time data for this study were adjusted to an individual dog body weight of 12 kg. The body weights of the dogs at time of dosing are tabulated in Table 25.

TABLE 25

Body Weight of dogs over the course of the study

| Animal No. | Sex | Bodyweight (kg) Study Day | | | | |
|---|---|---|---|---|---|---|
| | | −1 | 0 | 12 | 23 | 34 |
| 1 | M | 13.9 | 13.8 | 13.8 | 13.1 | 13.4 |
| 2 | M | 11.4 | 11.1 | 11.6 | 10.9 | 11.2 |
| 3 | M | 10.9 | 10.9 | 11.2 | 11.2 | 11.3 |
| 4 | M | 12.0 | 11.7 | 11.4 | 11.5 | 11.7 |
| 5 | M | 13.4 | 12.8 | 12.5 | 12.6 | 12.2 |
| 6 | M | 12.7 | 12.3 | 12.3 | 12.3 | 12.3 |

Statistical and Graphical Methodology

The data was summarized using descriptive statistics. Arithmetic means, standard deviations, and coefficients of variation were calculated for the pharmacokinetics parameters listed. For each parameter, the median, minimum and maximum values were presented. The mean, treatment and individual subject concentrations versus time profiles were also prepared.

Pharmacokinetic Results

The mean cinacalcet plasma pharmacokinetic parameters are presented in Table 26 (mean standard deviation and CV % values presented) and the mean cinacalcet plasma concentration versus time profile is presented in the FIGURE.

Comparison of 0.66 g (50 mg/g) (5% w/w) Cinacalcet Hydrochloride Nanoparticulate Dispersion (Trt A)/30 mg Cinacalcet (as 33 mg Cinacalcet Hydrochloride) Mimpara® Tablet (Trt B) Under Fasted Conditions (Dose Corrected)

The relative bioavailability of Trt A: 0.66 g (50 mg/g) (5% w/w) cinacalcet hydrochloride nanoparticulate dispersion compared to Trt B: 30 mg cinacalcet (as 33 mg cinacalcet hydrochloride) Mimpara® tablet was 962.284±577.486% based on $AUC_{last}$. The ratio of $C_{max}$ of Trt A: 0.66 g (50 mg/g) (5% w/w) cinacalcet hydrochloride nanoparticulate dispersion compared to Trt B: 30 mg cinacalcet (as 33 mg cinacalcet hydrochloride) Mimpara® tablet was 770.288±298.859%.

Comparison of 0.66 g (50 mg/g) (5% w/w) Cinacalcet Hydrochloride Nanoparticulate Dispersion (Trt C)/30 mg Cinacalcet (as 33 mg Cinacalcet Hydrochloride) Mimpara® Tablet (Trt D) Under Fed Conditions (Dose Corrected)

The relative bioavailability of Trt C: 0.66 g (50 mg/g) (5% w/w) cinacalcet hydrochloride nanoparticulate dispersion compared to Trt D: 30 mg cinacalcet (as 33 mg cinacalcet hydrochloride) Mimpara® tablet was 356.642±73.051% based on $AUC_{last}$. The ratio of $C_{max}$ of Trt C: 0.66 g (50 mg/g) (5% w/w) cinacalcet hydrochloride nanoparticulate dispersion compared to Trt D: 30 mg cinacalcet (as 33 mg cinacalcet hydrochloride) Mimpara® tablet was 276.563±126.703%.

Comparison of 0.66 g (50 mg/g) (5% w/w) Cinacalcet Hydrochloride Nanoparticulate Dispersion (Trt C)/0.66 g (50 mg/g) (5% w/w) Cinacalcet Hydrochloride Nanoparticulate Dispersion (Trt A) (Fed/Fasted Administration) (Dose Corrected)

The relative bioavailability of Trt C: 0.66 g (50 mg/g) (5% w/w) cinacalcet hydrochloride nanoparticulate dispersion compared to Trt A: 0.66 g (50 mg/g) (5% w/w) cinacalcet hydrochloride nanoparticulate dispersion was 106.202±27.861% based on $AUC_{last}$. The ratio of $C_{max}$ Trt C: 0.66 g (50 mg/g) (5% w/w) cinacalcet hydrochloride nanoparticulate dispersion compared to Trt A: 0.66 g (50 mg/g) (5% w/w) cinacalcet hydrochloride nanoparticulate dispersion was 84.489±50.460%.

Treatment C, 63.509±17.138 ng/mL·h following administration of Treatment A, 19.633±7.173 ng/mL·h following administration of Treatment D, and 9.973±6.040 ng/mL·h following administration of Treatment B respectively.

The maximum concentration determined was 25.207±9.933 ng/mL following administration of Treatment A, 17.676±5.167 ng/mL following administration of Treatment C, 7.172±2.741 ng/mL following administration of Treatment D and 3.799±2.279 ng/mL following administration of Treatment B respectively.

The median time to reach peak concentration was 1.0 h following administration of Treatments A, C and D and 1.75 h following administration of Treatment B respectively.

DISCUSSION & CONCLUSIONS

The biostudy was an open label, 4 treatments, 4 periods, unrandomised crossover study conducted in six dogs. The

TABLE 26

Mean Cinacalcet Plasma Pharmacokinetic Parameter Table

| PK Parameters* (Mean ± SD – CV %) | | Trt A: 0.66 g cinacalcet hydrochloride (50 mg/g) (5% w/w) NCD fasted (PO) N = 6 | Trt B: 30 mg cinacalcet (as 33 mg cinacalcet hydrochloride) Mimparae ® tablet fasted (PO) N = 6 | Trt C: 0.66 g cinacalcet hydrochloride (50 mg/g) (5% w/w) NCD fed (PO) N = 6 | | Trt D: 30 mg cinacalcet (as 33 mg cinacalcet hydrochloride) Mimpara ® tablet fed (PO) N = 6 |
|---|---|---|---|---|---|---|
| Relative Bioavailability (%) CV % | Based on $AUC_{last}$ | Comparison A/B 962.284 ± 577.486 60.0 | — | Comparison C/D 356.642 ± 73.051 20.5 | Comparison C/A 106.202 ± 27.861 26.2 | Comparison D/B* 275.152 ± 117.390 42.7 |
| Relative Bioavailability (%) CV % | Based on $AUC_{inf}$ | Comparison A/B 763.372 ± 329.598 43.2 | — | Comparison C/D 356.574 ± 60.690 17.0 | Comparison C/A 110.268 ± 28.757 26.1 | Comparison D/B* 231.997 ± 88.419 38.1 |
| Ratio Cmax (%) CV % | | Comparison A/B 770.288 ± 298.859 38.8 | — | Comparison C/D 276.563 ± 126.703 45.8 | Comparison C/A 84.489 ± 50.460 59.7 | Comparison D/B* 239.973 ± 145.072 60.5 |
| $AUC_{last}$ (ng/mL · hr) CV % | | 59.667 ± 15.926 26.7 | 8.265 ± 5.715 69.1 | 60.886 ± 14.619 24.0 | | 17.986 ± 6.917 38.5 |
| $AUC_{inf}$ (ng/mL · hr) CV % | | 63.509 ± 17.138 27.0 | 9.973 ± 6.040 60.6 | 67.088 ± 14.505 21.6 | | 19.633 ± 7.173 36.5 |
| $C_{max}$ (ng/mL) CV % | | 25.207 ± 09.933 39.4 | 3.799 ± 2.279 60.0 | 17.676 ± 5.167 29.2 | | 7.172 ± 2.741 38.2 |
| $T_{max}$ (hr) CV % | | 1.333 ± 0.983 73.7 | 1.667 ± 0.876 52.5 | 1.250 ± 0.987 79.0 | | 1.167 ± 0.258 22.1 |
| Median | | 1.00 | 1.75 | 1.00 | | 1.00 |
| Range | | 0.50-3.00 | 0.5-3 | 0.50-3.00 | | 1.00-1.50 |
| Thalf (hr) CV % | | 2.680 ± 1.537 57.4 | 1.726 ± 0.747 43.3 | 3.473 ± 1.159 33.4 | | 1.779 ± 0.557 31.3 |

*Corrected to a dog body weight of 12 kg

Comparison of 30 mg Cinacalcet (as 33 mg Cinacalcet Hydrochloride) Mimpara® Tablet (Trt D)/30 mg Cinacalcet (as 33 mg Cinacalcet Hydrochloride) Mimpara® Tablet (Trt B) (Fed/Fasted Administration) (Dose Corrected)

The relative bioavailability of Trt D: 30 mg cinacalcet (as 33 mg cinacalcet hydrochloride) Mimpara® tablet compared to Trt B: 30 mg cinacalcet (as 33 mg cinacalcet hydrochloride) Mimpara® tablet was 275.152±117.390% based on $AUC_{last}$. The ratio of $C_{max}$ of Trt D: 30 mg cinacalcet (as 33 mg cinacalcet hydrochloride) Mimpara® tablet compared to Trt B: 30 mg cinacalcet (as 33 mg cinacalcet hydrochloride) Mimpara® tablet was 239.973±145.072%.

The extent of absorption as determined by $AUC_{last}$ was 60.886±14.619 ng/mL·h following administration of Treatment C, 59.667±15.926 ng/mL·h following administration of Treatment A, 17.986±6.917 ng/mL·h following administration of Treatment D, and 8.265±5.715 ng/mL·h following administration of Treatment B respectively.

The extent of absorption as determined by $AUC_{inf}$ was 67.088±14.505 ng/mL·h was following administration of objective was to determine the pharmacokinetics of cinacalcet when administered orally as a cinacalcet hydrochloride (50 mg/g) (5% w/w) nanoparticulate dispersion and as a 33 mg cinacalcet (as hydrochloride) Mimpara® tablet to fasted and fed male beagle dogs.

The fasted administration of cinacalcet hydrochloride as a nanoparticulate dispersion formulation compared to a tablet was 9.6 fold higher in terms of AUC (Frel 962%) and 7.7 fold higher in terms of $C_{max}$ (Ratio $C_{max}$ 770%) (Trt A/B comparison). The fed administration of cinacalcet hydrochloride as a nanoparticulate dispersion formulation compared to a tablet was 3.6 fold higher in terms of AUC (Frel 357%) and 2.8 fold higher in terms of $C_{max}$ (Ratio $C_{max}$ 277%) (Trt C/D comparison).

The food effect of cinacalcet hydrochloride documented in the literature was observed when Mimpara® tablets were administered under fasted and fed conditions (Trt D/B comparisons). There was a 2.7 fold increase in AUC (Frel 275%) and a 2.3 fold increase in $C_{max}$ (Ratio $C_{max}$ 240%). However, when the impact of food was evaluated following administration of the nanoparticulate dispersion formulation according to the invention, the mean AUC values were comparable (Frel 106%) and the mean $C_{max}$ values were slightly lower (Ratio $C_{max}$ 84%).

Summarising then, the administration of cinacalcet hydrochloride as a nanoparticulate dispersion formulation resulted in a significant increase in the rate ($C_{max}$) and extent (AUC) of absorption under fasted conditions and to a lesser extent under fed conditions. In addition, the administration of cinacalcet hydrochloride as an nanoparticulate dispersion formulation resulted in a negation of the food effect which was observed with administration of the drug in tablet form. All treatments were well tolerated in this dog population.

This example demonstrates the increased bioabilability obtained with a nanoparticulate cinacalcet composition according to the invention as compared to a known, non-nanoparticulate cinacalcet composition. In addition, this example demonstrates that nanoparticulate cinacalcet compositions according to the invention exhibit a reduced food effect (i.e., difference in absorption when administered under fed as compared to fasting conditions) as compared to the food effect observed with a known, non-nanoparticulate cinacalcet composition.

It will be apparent to those skilled in the art that various modifications and variations can be made in the methods and compositions of the present inventions without departing from the spirit or scope of the invention. Thus, it is intended that the present invention cover the modification and variations of the invention provided they come within the scope of the appended claims and their equivalents.

What is claimed is:

1. A stable nanoparticulate cinacalcet composition comprising:
   (a) solid particles of cinacalcet or a pharmaceutically acceptable salt thereof having an effective average particle size of less than about 2000 nm; and
   (b) at least one surface stabilizer.

2. The composition of claim 1, wherein the cinacalcet or salt thereof is in a crystalline phase, an amorphous phase, a semi-crystalline phase, or mixtures thereof.

3. The composition of claim 1, wherein the effective average particle size of the solid particles of cinacalcet or a salt thereof is selected from the group consisting of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less, less than about 800 nm, less than about 700 nm, less than about 600 nm, less than about 500 nm, less than about 400 nm, less than about 300 nm, less than about 200 nm, less than about 150 nm, less than about 100 nm, less than about 75 nm, and less than about 50 nm.

4. The composition of claim 1, wherein the composition is formulated:
   (a) for administration selected from the group consisting of oral, pulmonary, intravenous, rectal, ophthalmic, colonic, parenteral, intracisternal, intravaginal, intraperitoneal, local, buccal, nasal, and topical administration;
   (b) into a dosage form selected from the group consisting of liquid dispersions, gels, aerosols, ointments, creams, tablets, sachets and capsules;
   (c) into a dosage form selected from the group consisting of lyophilized formulations, fast melt formulations, controlled release formulations, delayed release formulations, extended release formulations, pulsatile release formulations, and mixed immediate release and controlled ase formulations; or
   (d) any combination (a) (b), and (c).

5. The composition of claim 1, comprising a primary surface stabilizer and at least one secondary surface stabilizer.

6. The composition of claim 1, wherein at least one surface stabilizer is selected from the group consisting of a non-ionic surface stabilizer, an ionic surface stabilizer, an anionic surface stabilizer, a cationic surface stabilizer, and a zwitterionic surface stabilizer.

7. The composition of claim 1, wherein at least one surface stabilizer is selected from the group consisting of copolymers of vinylpyrrolidone and vinyl acetate or copovidone, docusate sodium, hydroxypropylcellulose, hydroxypropylmethylcellulose, polyoxyethylene sorbitan fatty acid esters, block copolymers based on ethylene oxide and propylene oxide, polyvinylpyrrolidone, deoxycholic acid sodium salt, sodium lauryl sulphate, benzalkonium chloride, lecithin, distearyl palmitate glyceryl, albumin, lysozyme, gelatin, macrogol 15 hydroxystearate, tyloxapol and polyethoxylated castor oil.

8. The composition of claim 1, wherein the cinacalcet salt is cinacalcet hydrochloride.

9. The composition of claim 1, wherein the composition exhibits improved bioavailability as compared to a known non-nanoparticulate cinacalcet composition.

10. The composition of claim 1, wherein:
   (a) the $T_{max}$ of the nanoparticulate cinacalcet composition, when assayed in the plasma of a mammalian subject following administration, is less than the $T_{max}$ for a non-nanoparticulate composition of the same cinacalcet, administered at the same dosage;
   (b) the $C_{max}$ of the nanoparticulate cinacalcet composition, when assayed in the plasma of a mammalian subject following administration, is greater than the $C_{max}$ for a non-nanoparticulate composition of the same cinacalcet, administered at the same dosage;
   (c) the AUC of the nanoparticulate cinacalcet composition, when assayed in the plasma of a mammalian subject following administration, is greater than the AUC for a non-nanoparticulate composition of the same cinacalcet, administered at the same dosage; or
   (d) any combination of (a), (b) and (c).

11. The composition of claim 1 which does not produce significantly different absorption levels when administered under fed as compared to fasting conditions.

12. The composition of claim 11, wherein the difference in absorption of the active agent composition of the invention, when administered in the fed versus the fasted state, is selected from the group consisting of less than about 100%, less than about 90%, less than about 80%, less than about 70%, less than about 60%, less than about 50%, less than about 40%, less than about 30%, less than about 25%, less than about 20%, less than about 15%, less than about 10%, less than about 5%, and less than about 3%.

13. The composition of claim 1, wherein administration of the composition to a human in a fasted state is bioequivalent to administration of the composition to a subject in a fed state.

14. The composition of claim 13, wherein "bioequivalency" is established by:
   (a) a 90% Confidence Interval of between 0.80 and 1.25 for both $C_{max}$ and AUC; or
   (b) a 90% Confidence Interval of between 0.80 and 1.25 for AUC and a 90% Confidence Interval of between 0.70 to 1.43 for $C_{max}$.

15. A method of making a nanoparticulate cinacalcet, or a pharmaceutically acceptable salt thereof, composition comprising contacting solid particles of a cinacalcet with at least one surface stabilizer for a time and under conditions sufficient to provide a composition comprising solid particles of cinacalcet having an effective average particle size of less than about 2000 nm.

16. A method of treating a mammal in need comprising administering a stable nanoparticulate cinacalcet composition comprising:
   (a) solid particles of cinacalcet or a pharmaceutically acceptable salt thereof having an effective average particle size of less than about 2000 nm; and
   (b) at least one surface stabilizer.

17. The method of claim 16, wherein the composition is useful in treating hyperthyroidism, hypercalcemia, hyperparathyroidism, parathyroid carcinoma, or a combination thereof.

* * * * *